United States Patent
Linnes et al.

(10) Patent No.: US 12,115,529 B2
(45) Date of Patent: *Oct. 15, 2024

(54) TEMPERATURE CONTROLLED VALVES FOR PAPER-BASED MICROFLUIDIC SYSTEMS

(71) Applicant: Purdue Research Foundation, West Lafayette, IN (US)

(72) Inventors: Jacqueline C. Linnes, West Lafayette, IN (US); Megan Zaiyi Chiu, West Lafayette, IN (US); Rui Shen, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/135,073

(22) Filed: Apr. 14, 2023

(65) Prior Publication Data
US 2023/0249175 A1   Aug. 10, 2023

Related U.S. Application Data

(60) Continuation of application No. 17/402,496, filed on Aug. 13, 2021, now Pat. No. 11,628,434, which is a
(Continued)

(51) Int. Cl.
*C12Q 1/6844* (2018.01)
*B01L 3/00* (2006.01)
(Continued)

(52) U.S. Cl.
CPC ........... *B01L 3/5027* (2013.01); *B01L 3/5023* (2013.01); *B01L 7/52* (2013.01); *C12Q 1/6846* (2013.01);
(Continued)

(58) Field of Classification Search
CPC ....... B01L 2300/0825; B01L 2300/126; B01L 2300/1827; B01L 2400/0677
See application file for complete search history.

(56) References Cited

U.S. PATENT DOCUMENTS

| | | | |
|---|---|---|---|
| 11,090,649 B2 * | 8/2021 | Linnes | B01L 3/5027 |
| 11,529,626 B2 * | 12/2022 | Linnes | B01L 7/52 |
| 2016/0002621 A1 * | 1/2016 | Nelson | C12N 15/1006 |
| | | | 435/91.21 |

FOREIGN PATENT DOCUMENTS

WO    WO-2017014828 A2 *   1/2017

OTHER PUBLICATIONS

Rivas et al., "Improving sensitivity of gold nanoparticle-based lateral flow assays by using wax-printed pillars as delay barriers of microfluidics," Lab Chip, published September, vol. 14, pp. 4406-4414. (Year: 2014).*

* cited by examiner

*Primary Examiner* — Young J Kim
(74) *Attorney, Agent, or Firm* — Piroozi-IP, LLC

(57) ABSTRACT

The present invention relates to a low-cost, thermally reversible valve for paper-fluidic diagnostic devices. In particular, this invention demonstrates a tunable valve mechanism fabricated by wax-ink printing and localized heating via thin-film resistors to sequentially release liquids through a cellulose or nitrocellulose membrane. The wax-ink valve can obstruct fluid flow for a sustained time and are thermally actuated to release a controlled amount of liquid past the valve. This integrated paper-fluidic diagnostic assay device requires minimal user involvement, can be easily manufactured and tuned to meet various fluid delivery timing and incubation needs.

12 Claims, 14 Drawing Sheets

Related U.S. Application Data division of application No. 16/094,898, filed as application No. PCT/US2017/028237 on Apr. 19, 2017, now Pat. No. 11,090,649.

(60) Provisional application No. 62/324,453, filed on Apr. 19, 2016.

(51) Int. Cl.
| | |
|---|---|
| *B01L 7/00* | (2006.01) |
| *C12Q 1/70* | (2006.01) |
| *F16K 99/00* | (2006.01) |
| *G01N 33/543* | (2006.01) |
| *G01N 33/558* | (2006.01) |

(52) U.S. Cl.
CPC .......... *C12Q 1/703* (2013.01); *F16K 99/0032* (2013.01); *F16K 99/0036* (2013.01); *G01N 33/54388* (2021.08); *G01N 33/558* (2013.01); *B01L 2300/0825* (2013.01); *B01L 2300/126* (2013.01); *B01L 2300/1827* (2013.01); *B01L 2400/0406* (2013.01); *B01L 2400/0677* (2013.01); *G01N 2333/005* (2013.01); *G01N 2333/195* (2013.01); *Y02A 50/30* (2018.01)

(A)

(B)

A.
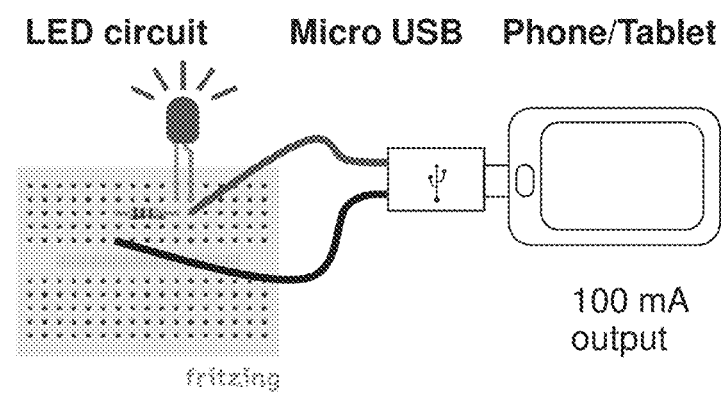
B.
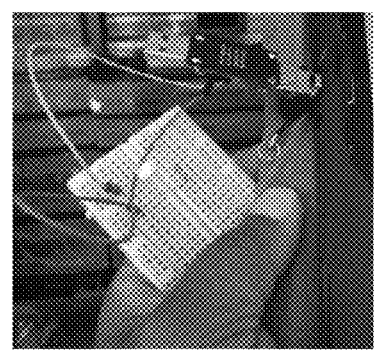
FIG. 14A
FIG. 14B
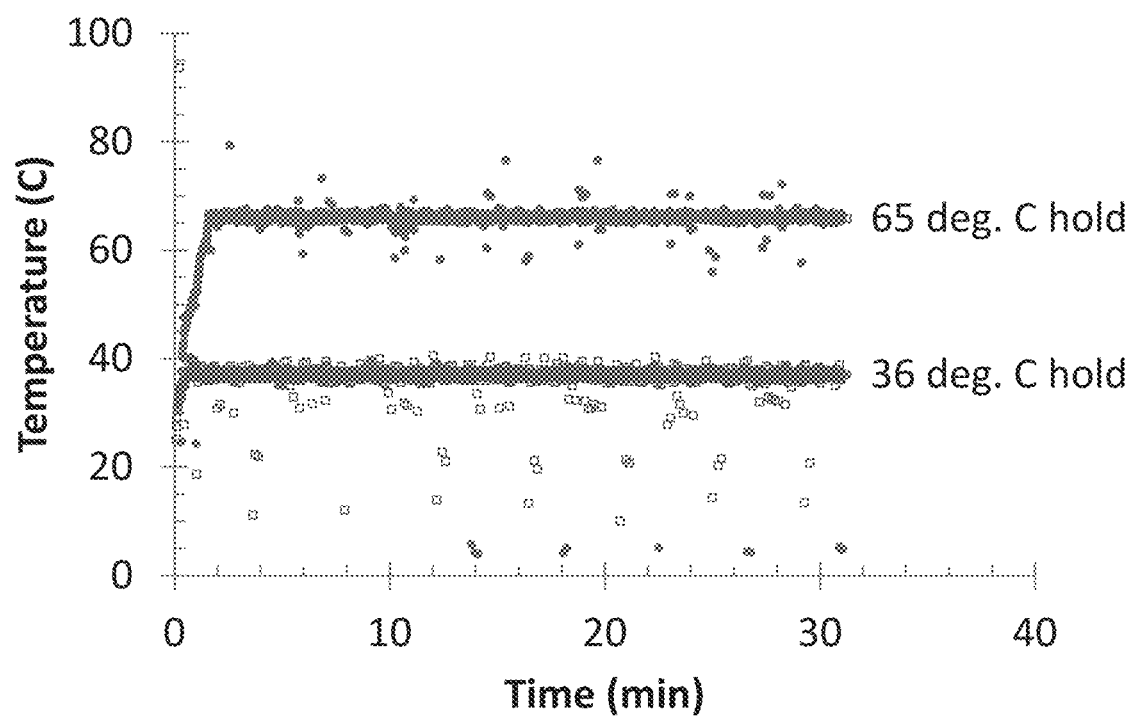
Fig. 15

TEMPERATURE CONTROLLED VALVES FOR PAPER-BASED MICROFLUIDIC SYSTEMS

CROSS REFERENCE

This application is continuation application of U.S. Non-Provisional application having Ser. No. 17/402,496 which was filed Aug. 13, 2021, which is a divisional application of U.S. Non-Provisional application having Ser. No. 16/094,898 which was filed on Oct. 19, 2018, now U.S. Pat. No. 11,090,649 to Linnes et al., which is a national stage entry under 35 U.S.C. § 371(b) of International Application No. PCT/US17/28237 filed on Apr. 19, 2017, which claims priority under 35 U.S.C. § 119(e) to the U.S. Provisional Application No. 62/324,453, filed on Apr. 19, 2016, the content of each of which is hereby incorporated by reference in their entirety into the present disclosure.

TECHNICAL FIELD

The present invention generally relates to temperature-controlled valves for paper-based microfluidic systems and more specifically to thermally reversible phase-change valves for controlling fluid flow in a paper-based microfluidic system.

BACKGROUND

This section introduces aspects that may help facilitate a better understanding of the disclosure. Accordingly, these statements are to be read in this light and are not to be understood as admissions about what is or is not prior art.

Advances in microfluidic control and biochemical detection methods have enabled a multitude of lab-on-chip assays for rapid point-of-care diagnostics including immunoassays, enzyme assays, nucleic acid amplification and detection, and whole cell analysis (J. Park, et al., *Anal. Chem.*, 2012, 84, 2133-2140; S. Lindstrom, et al., *Lab Chip*, 2010, 10, 3363-3372). While these traditional microfluidic devices non-invasively analyze small volume samples, their global usage, particularly in low-resource settings, is limited by expensive instrumentation requirements and high costs of consumable assay cartridges (J. Hu, et al., *Biosens. Bioelectron.*, 2014, 54, 585-597). With low manufacturing costs and no external instrumentation, paper-fluidic diagnostics such as dipstick assays and lateral flow immunoassays (LFIAs) have been widely adopted for point-of-care testing and disease screening throughout the world. Both colorimetric dipstick assays and LFIAs rapidly capture and detect target analytes through a single user step, delivering a liquid sample to reagents pre-embedded in the pores via capillary action. Mechanisms to direct and redirect fluid flow are essential for paper-fluidic diagnostics to accomplish multi-step bioassays performed within lab-on-chip platforms, and have been a primary research focus for the past ten years. Also referred to as paper-based analytical devices (PADs) in the literature, paper-fluidics have improved, but not yet achieved, the precisely timed delivery of liquids that is characteristic of lab-on-chip assays.

Paper-fluidic devices will only be an appropriate alternative to complex lab-on-chip assay platforms when greater fluidic control can be achieved within the membranes. The sophisticated fluid transport including mixing, separating, and timed delivery of liquids performed in lab-on-chip devices can be achieved by incorporating three fundamental elements: pumps, routers, and valves. Rather than actively pump fluid through open channels, paper-fluidic devices leverage the inherent wicking ability of porous materials to transport fluid through multiple reagent zones. By eliminating the external pumping mechanism that microfluidic devices typically require, paper-fluidic devices are a much more portable alternative. Routers directing flow through channels can be defined by hydrophobic barriers made from PDMS, tape, and/or wax-ink (A. W. Martinez, et al., *Lab Chip*, 2010, 10, 2499-2504; C. Renault, et al., *Langmuir*, 2014, 30, 7030-7036).

However, valves that obstruct and control the release of fluid remain the most challenging element to incorporate into paper-based devices. A valve mechanism that completely obstructs fluid flow for a sustained amount of time and requires minimal user involvement has been difficult to engineer thus far.

SUMMARY OF THE INVENTION

In some aspects, this present invention relates to a low-cost valve for paper-fluidic diagnostic devices that requires minimal user involvement, can be easily manufactured, can be tuned to meet various fluid delivery timing and incubation needs, and can be actuated multiple times. In particular, this invention demonstrates a novel, tunable valve mechanism fabricated by wax-ink printing and localized heating via thin-film resistors to sequentially release liquids through a nitrocellulose membrane. The wax-ink valves fully obstruct fluid flow for a sustained time and are thermally actuated to release a controlled amount of liquid past the valve.

In one aspect of the present invention there is provided an assay device comprising a porous hydrophilic substrate and an at least one thermally reversible barrier, wherein the thermally reversible barrier defines an assay area. The porous hydrophilic substrate may comprise cellulose, polyether sulfone, nitrocellulose acetate, cellulose acetate or a combination thereof and the thermally reversible barrier comprises a phase change material such as agarose, wax, fatty acids or combinations thereof.

In another aspect of the present invention there is provided a method for testing a sample for the presence or absence of a nucleic acid comprising the steps of providing an assay device comprising a porous hydrophilic substrate comprising a sample application area, an amplification area and a detection area wherein the sample application area and amplification area are separated by a first thermally reversible barrier and the amplification area and detection area are separated by a second thermally reversible barrier, applying a sample to the sample application area, heating the first thermally reversible barrier to a temperature at or above the melting temperature of the first thermally reversible barrier allowing the sample to flow from the extraction area to the amplification area, lowering the temperature of the first thermally reversible barrier to a temperature lower than the melting point of the first thermally reversible barrier blocking the flow of the sample from the amplification area back into the sample application area, amplifying a nucleic acid in the sample, heating the second thermally reversible barrier to a temperature at or above the melting temperature of the barrier allowing the sample to flow from the amplification area to the detection area and detecting the presence or absence of the nucleic acid in the sample.

BRIEF DESCRIPTION OF THE FIGURES

These and other features, aspects and advantages of the present invention will become better understood with reference to the following figures, associated descriptions and claims.

FIG. 8A demonstrates the length of time (diamonds) required to actuate valves decreases with increased current while the valve actuation temperature (squares) remained approximately 48° C. (NC, nitrocellulose, closed symbol) and 41° C. (Chr1, cellulose, open symbol). FIG. 8B shows the length of heating time required to release fluid through a valve increased with valve width, however, valves greater than 1 mm (nitrocellulose) and 10 mm (cellulose) wide are impassible (n=3). FIG. 8C shows representative images of fluid flow in the nitrocellulose and cellulose membranes showing minimum valve widths that allowed flow (0.1, 1 mm) and that were too wide to allow fluid to pass (4, 10 mm). FIG. 8D shows additional heating of a 0.1 mm (nitrocellulose) and 1 mm (cellulose) valve does not increase the amount of fluid passing through the valve. More fluid can wick through open valves on cellulose than nitrocellulose but with greater variance (n=3). Error bars indicate standard error.

FIG. 9A shows the images and FIG. 9B depicts the temperature profile of valve on nitrocellulose. At step (1), blue liquid is added to the membrane and flows through the open valve at step (2). At step (3) upon heating, the valve closes. At step (4), red liquid is added to the membrane as the valve cools. In step (5), this liquid is blocked by the closed valve. When re-heated, the valve opens to allow the red fluid to pass at step (6).

FIG. 11A shows the recorded images; FIG. 11B depicts the normalized test line intensity of E. coli detection in standard single-step LFIAs (S) and gold enhanced multi-step LFIAs (E). Gold enhancement improves visible signal intensity up to 6× as compared to the standard single-step LFIA. * indicates p<0.05, n=3 (LFIA: lateral flow immunoassay).

FIGS. 14A and 14B shows mobile phone power harvesting. FIG. 14A depicts a schematic of the power harvesting set up. FIG. 14B is a photograph of an LED lighting up from power harvested from an android tablet.

FIG. 15 demonstrates a consistent temperature control of a small printed silver-ink resistor on a paper substrate for 30 min using power harvested from an android tablet.

DETAILED DESCRIPTION

Figure 1:
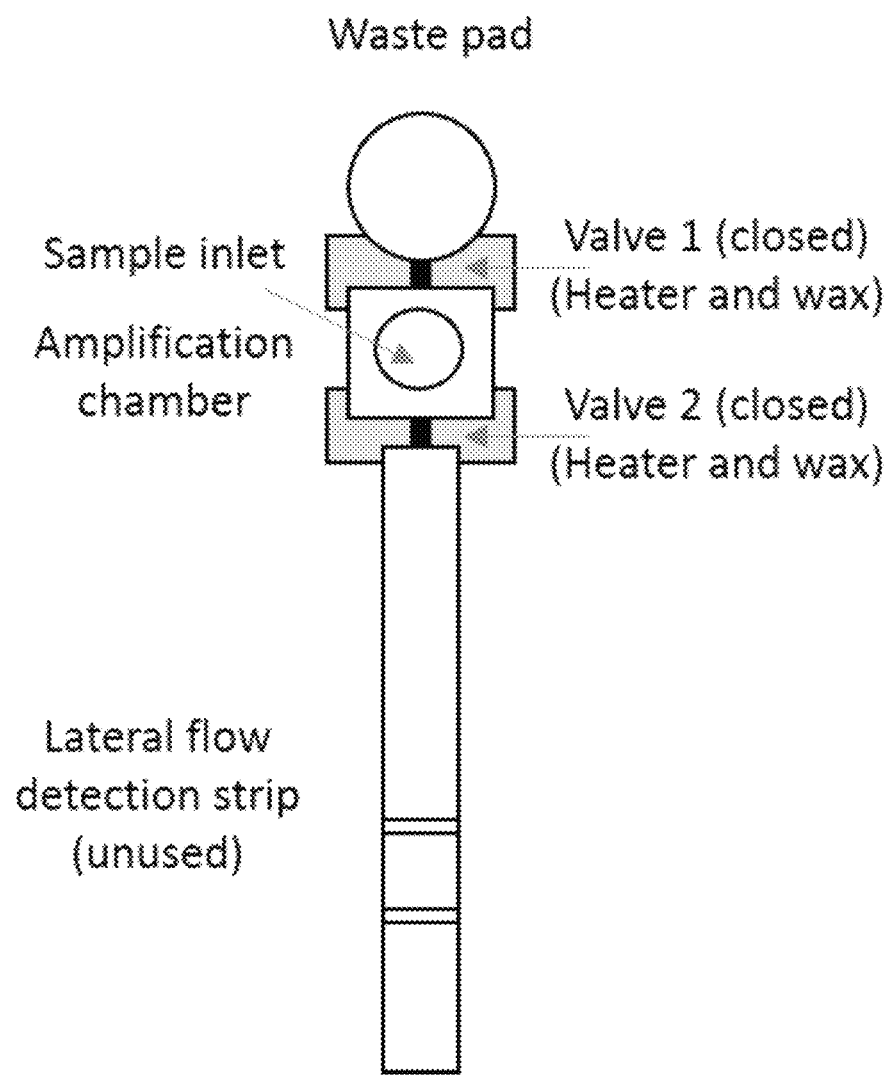
FIG. 1 is a schematic showing an assay device and method of use according to one aspect of the present invention.
Figure 1:
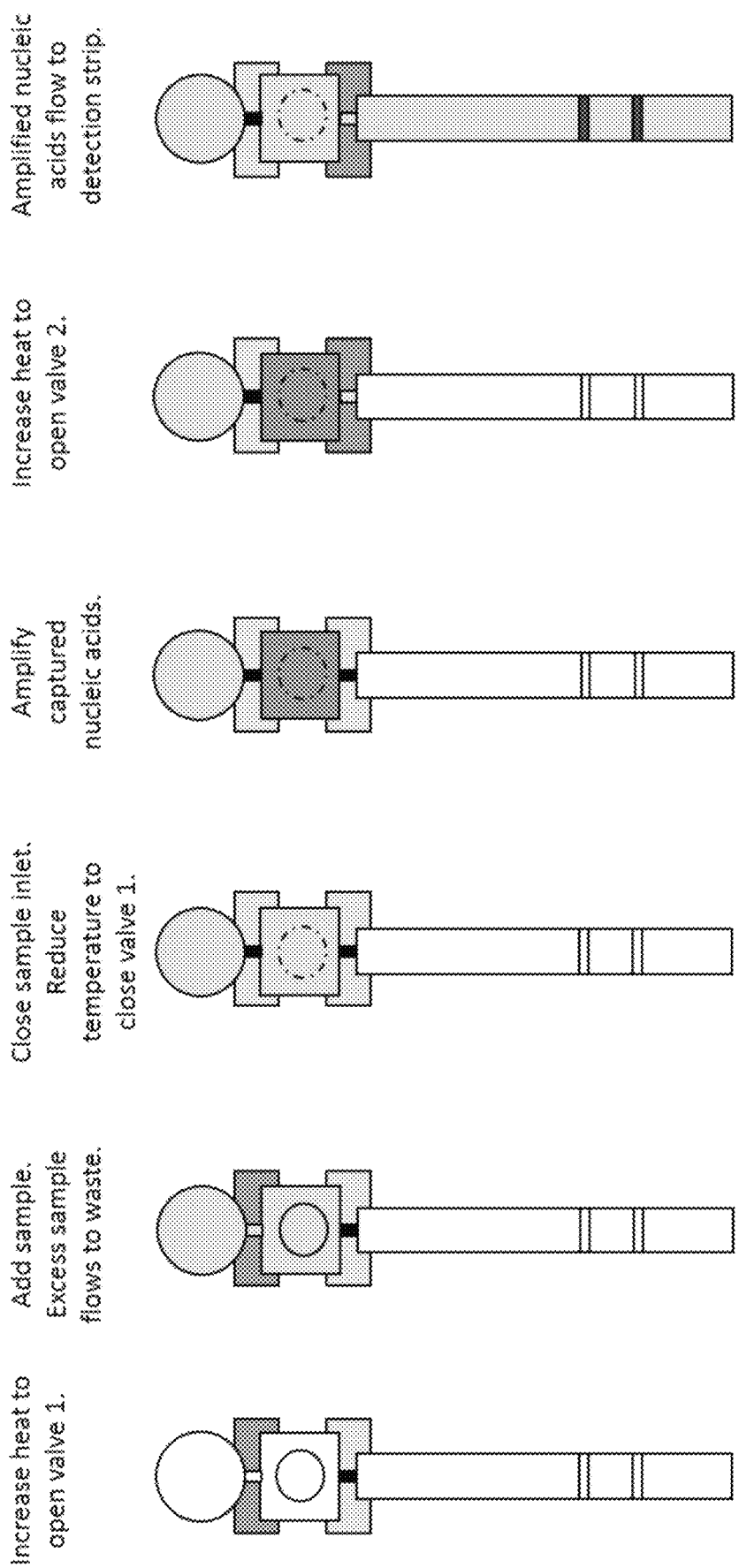

For the purposes of promoting an understanding of the principles of the present disclosure, the following detailed description is of the best currently contemplated modes of carrying out the invention. The description is not to be taken in a limiting sense, but is made merely for illustrating the general principles of the invention, since the scope of the invention is best defined by the appended claims.

Values expressed in a range format should be interpreted in a flexible manner to include not only the numerical values explicitly recited as the limits of the range, but also to include all the individual numerical values or sub-ranges encompassed within that range as if each numerical value and sub-range were explicitly recited. In the present disclosure the term "about" can allow for a degree of variability in a value or range, for example, within 10%, within 5%, or within 1% of a stated value or of a stated limit of a range. In the present disclosure the term "substantially" can allow for a degree of variability in a value or range, for example, within 80%, within 90%, within 95%, or within 99% or more of a stated value or of a stated limit of a range.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting. Information that is relevant to a section heading may occur within or outside of that particular section.

Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

Broadly, the present invention provides an assay device having a porous hydrophilic substrate and at least one thermally reversible barrier. When closed, the thermally reversible barrier prevents a sample from freely moving along the porous hydrophobic substrate and further defines discrete areas on the hydrophilic porous surface. The thermally reversible barrier is controlled by heat, melting at higher temperatures to allow the flow of a sample liquid on the porous hydrophilic substrate from one area to another and blocking the flow of sample liquid when re-solidified at lower temperatures.

The assay device of the present system is advantageous because it utilizes a thermally reversible barrier that is simple to use to control the flow of a sample liquid on the porous hydrophilic substrate. Paper-based microfluidic assays, particularly for nucleic acid detection, are well known in the art. However, to date, paper-based valves/barriers that facilitate fluidic control are not compatible with the extended temperatures and times required for nucleic acid amplification. In contrast, the thermally reversible barriers of the present invention may be used on the porous substrate itself to control fluidics by stopping or starting sample fluid flow sample capture, isothermal amplification and detection.

In one aspect of the present invention there is provided an assay device comprising a porous substrate. The porous substrate is such that it allows for the flow or movement of an aqueous sample along the porous substrate. It is contemplated that the aqueous sample is a biological sample such as, but not limited to, a blood sample. The porous substrate may be, but not limited to, cellulose, polyether sulfone, nitrocellulose, cellulose acetate, glass fibers, polycarbonate, or any combination of these. In a non-limiting example the porous hydrophilic substrate is cellulose or nitrocellulose. In another aspect of the present invention porous hydrophilic substrate may comprise any shape, but preferably is an elongated strip. It may be square, rectangular or the porous hydrophilic substrate may comprise areas separated by smaller channels for moving a sample from one area to another.

In another aspect of the present invention the assay device comprises a thermally reversible barrier, where the thermally reversible barrier may define an assay area on the porous hydrophilic substrate. The thermally reversible barrier forms a fluid impermeable barrier when in a solid state, preventing the sample from moving along the porous hydrophilic substrate. Upon heating of the thermally reversible barrier to a temperature at or above the melting temperature of the material of the thermally revisable barrier, the barrier becomes more fluid, allowing for the flow of the sample along the porous hydrophilic substrate. When the heat is removed and the temperature is below the melting temperature of the thermally reversible barrier, the flow of the sample along the porous hydrophilic substrate is impeded or blocked.

The thermally reversible barrier may comprise any material that blocks the flow of the sample at a temperature below the melting temperature of the material and conversely, allow the flow of the sample on the porous hydrophilic substrate when the temperature is above the melting temperature of the sample. The material of the thermally reversible barrier has a melting temperature compatible with the stability of the sample. It is appreciated that the melting temperature should not be so high that there is degradation of the sample at that temperature. The thermally reversible barrier of the present invention may comprise agarose, paraffin (wax), lipids, fatty acids, poly(N-isoproylacrylamide), gelatin, peptides, oligonucleotides, other phase-change materials as either the polymerized or crosslinking subunits or a combination thereof. Phase-change materials are commonly known in the art with organic phase change materials being comprised of paraffin and/or fatty acids and many are commercially available. A non-limiting example of a commercially available material is biobased PureTemp (Entropy Solutions LLC, Plymouth, MN). PureTemp 68 is particularly advantageous for use with biological samples having a melting temperature of about 68° C. It is appreciated that the melting temperature of the material of the thermally reversible barrier comprising fatty acids, peptides, or oligonucleotides, may be controlled by the average chain length of the monomer composition.

Figure 2:
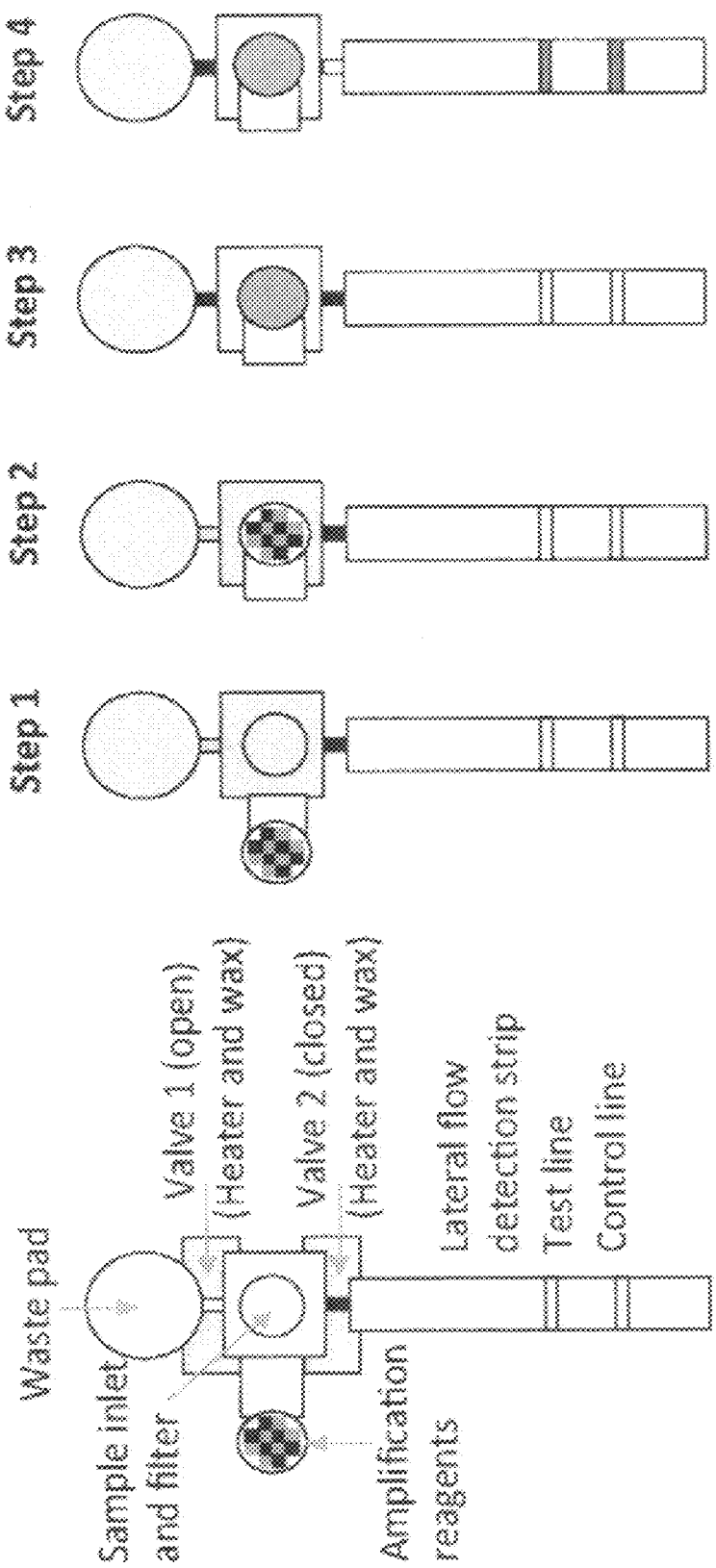
FIG. 2 is a schematic showing an assay device and method of use according to another aspect of the present invention.

In a further aspect of the present invention the assay device comprises a plurality of assay areas defined by a plurality of thermally reversible barriers. In one non-limiting example of the present invention, the assay device comprises a sample inlet/amplification area, a waste pad and a detection area (FIGS. 1 and 2). The sample inlet/amplification area is separated from the waste pad by a first thermally reversible barrier (valve 1). The sample inlet/amplification area is further separated from the detection area by a second reversible thermal barrier (valve 2). In an alternate non-limiting example of the present invention, the assay device comprises a sample application/extraction area, an amplification/reaction area and a detection area. The sample/extraction area and amplification area are separated by a first thermally reversible barrier and the amplification area and detection areas are separated by a second thermally reversible barrier. Additionally, the assay device of the present invention may comprise an additional area comprising the reagents necessary for amplification of the sample. This reagent area is adjacent to, and separated from, the amplification area by a third thermally reversible barrier. Alternatively, the reagent area may be separated from the amplification area by other means and contacted to the amplification area by a means other than a thermally reversible barrier (FIG. 2).

In a further aspect of the present invention, the plurality of the thermally reversible barriers may all comprise the same material or they may comprise different materials. State alternatively, the thermally reversible barriers may all have the sample melting temperature or one or more may have different melting temperatures. It is appreciated that there may be an advantage to having different barriers with different melting temperatures, particularly if the barriers are physically close to one another and one barrier is open to sample flow while another remains closed to sample flow.

The present invention also provides methods of using the assay device of the present invention. The method involves the detection of a chemical or biological molecule such as, but not limited to, nucleic acid. Alternatively, the biological molecule may be a cell, an antibody, a protein, a hormone, a coenzyme or any molecule of interest. Methods using the assay device of the present invention may be tailored to detecting the presence of viruses such as HIV, influenza, tobacco mosaic virus, bacteria including *Vibrio cholerae, Escherichia coli, Klepsiella pneumonia, Bacillus anthracis, Staphylococcus auerus*, etc., and C-reactive protein, cytokines and inflammatory markers, or tumor antigens. Moreover, the assay device may be tailored to detect a non-biological sample such as, but not limited to a toxic chemical, illicit substance, or heavy metal.

In one aspect of the present invention, the method comprises the step of providing the assay device comprising a porous substrate comprising a sample application area, an amplification area and a detection area wherein the sample application area and amplification area are separated by a first thermally reversible barrier and the amplification area and detection area are separated by a second thermally reversible barrier. A sample of interest is then applied to the sample application area. In one aspect of the present invention, the assay device further comprises a waste area wherein the waste area is separated from the sample addition area by a fourth thermally reversible barrier. (FIGS. 1 and 2). When the sample is being applied, the temperature of the fourth thermally reversible barrier is heated to a temperature above the melting temperature of the material of the fourth thermally reversible barrier, allowing an excess sample to flow from the sample application area to the waste area.

After the sample is added, the temperature of the fourth thermally reversible barrier is lowered below the melting point of the material of the barrier, blocking the backflow of the sample in the waste area into the sample amplification area.

After the sample is applied, the first thermally reversible barrier is heated to a temperature at or above the melting temperature of the first thermally reversible barrier allowing the sample to flow from the extraction area to the amplification area. After the sample has flowed to the amplification area, the temperature of the first thermally reversible barrier is lowered to a temperature lower than the melting point of the first thermally reversible barrier, thereby solidifying the barrier and blocking the flow of the sample from the amplification area back into the sample application area.

In another aspect of the present invention the temperature of the thermally reversible barrier is increased to at least the melting temperature of the material of the thermally reversible barrier by applying heat. The source of this heat may be, by way of non-limiting example, a hot plate, a resistive wire, resistive ink, electrode, oven, thermoelectric heating, inductive heating, or exothermic chemical reactions. The thermally reversible barrier is allowed to cool to a temperature below the melting temperature of the material of the thermally reversible barrier by removal of the heat. The cooling may be passive or it may be active. Passive cooling may be accomplished by removing the heat source and allowing the thermally reversible barrier to cool. Alternatively, the thermally reversible barrier may be cooled by actively cooling the barrier. Methods may include using an endothermic chemical reaction, a heat sink, a coolant, refrigeration, evaporation, conduction or thermoelectric cooling. By way of non-limiting example, if the thermally reversible barrier is PureTemp 68, then the thermally reversible barrier blocks the flow of the sample fluid when the thermally reversible barrier is at a temperature below 68° C. As the thermally reversible barrier is heated to a temperature at or greater than about 68° C., the barrier begins to melt, allowing the sample fluid to flow across the barrier. When the temperature is then allowed to drop below about 68° C. the barrier transitions to a solid phase, again blocking the flow of the sample fluid.

After the sample has been transferred from the sample application area to the amplification area, the biological molecule of interest in the sample is amplified. In the case of biological molecules such as nucleic acid, the amplification area may be heated to a temperature of about 65° C. The temperature and time required for amplification depends on the molecules in the sample to be amplified. In one aspect of the present invention, the reagents necessary for the amplification of the biological molecule are present in the amplification area before the addition of the sample. In an alternate example of the present invention, the assay device further comprises an amplification reagent area where the amplification reagent area is adjacent to the amplification area and separated from the amplification area by a third thermally reversible barrier. After the sample is transferred from to the amplification area, heat is applied to the third thermally reversible barrier, increasing the temperature of the barrier to at or above the melting temperature of the material of the third thermally reversible barrier, allowing the amplification reagents to flow from the amplification reagent area into the amplification area. Alternately, there is no thermally reversible barrier between the amplification reagent area and the amplification area. The reagents in the amplification reagent area are transferred to the amplification area by folding of moving the amplification reagent area to the amplification area (FIG. 2, step 2).

After the desired molecules have been amplified, the second thermally reversible barrier is heated to a temperature at or above the melting temperature of the barrier allowing the sample to flow from the amplification area to the detection area and detecting the presence or absence of the molecule of interest in the amplified sample. Detection of the molecule of interest may be qualitative and/or quantitative.

In a further aspect of the present invention, methods are provided for using the assay device of the present invention to perform multi-step chemical reactions, particularly where the reaction needs to be incubated with at least one substrate and the product of that reaction incubated with another in order to detect the original molecular target. An example of this would be enzymatic signal amplification using horseradish peroxidase to detect an antibody-protein conjugation wherein the binding of a first antibody and protein in a sample may occur in a first area of the assay device. A thermally reversible barrier separating the first area from a second area is then opened to allow the sample to flow to a second area of the assay device wherein horseradish peroxidase can amplify the signal and the product detected in a second area of the assay device.

In some illustrative embodiments, this present invention relates to an assay device comprising a porous substrate and at least one thermally reversible barrier, wherein the thermally reversible barrier defines an assay area.

In some illustrative embodiments, this present invention relates to an assay device disclosed herein wherein the porous substrate comprises cellulose, polyether sulfone, nitrocellulose, cellulose acetate, glass fiber, or a combination thereof.

In some illustrative embodiments, this present invention relates to an assay device comprising a plurality of thermally reversible barriers and a plurality of assay areas.

In some illustrative embodiments, this present invention relates to an assay device comprising a plurality of thermally reversible barriers, a plurality of assay areas, and a plurality of heating and temperature control components.

In some illustrative embodiments, this present invention relates to an assay device comprising a plurality of thermally reversible barriers, a plurality of assay areas, a plurality of heating and temperature control components, and a means of controlling local temperature of the assay device using a conductive ink printed resistor.

In some illustrative embodiments, this present invention relates to an assay device wherein the conductive ink printed resistor is made of silver, carbon, or gold ink.

In some illustrative embodiments, the assay device disclosed herein further comprising a means of controlling local temperature of the assay device using a conductive ink printed resistor.

In some illustrative embodiments, this present invention relates to an assay device wherein the assay area comprises a sample application area, an amplification area, a detection area, an absorbent pad (or sink), or a combination thereof.

In some illustrative embodiments, this present invention relates to an assay device wherein a thermally reversible barrier is positioned between the sample application area and a waste pad and a second thermally reversible barrier is positioned between the sample application area and the detection area.

In some illustrative embodiments, this present invention relates to an assay device wherein each thermally reversible barrier is equipped with a set of heating and temperature control components.

In some illustrative embodiments, this present invention relates to an assay device comprising a plurality of thermally reversible barriers a plurality of assay areas, and an amplification reagent area, the amplification reagent area being adjacent to the amplification area and being separated from the amplification area by an additional thermally reversible barrier.

In some illustrative embodiments, this present invention relates to an assay device comprising a plurality of thermally reversible barriers a plurality of assay areas, an amplification reagent area wherein the amplification reagent area being adjacent to the amplification area and being separated from the amplification area by an additional thermally reversible barrier, and heating and temperature control components for the additional thermally reversible barrier.

In some illustrative embodiments, this present invention relates to an assay device wherein the thermally reversible barrier closes to stop a fluid applied to the porous substrate substantially from flowing from one assay area to another when the thermally reversible barrier is heated to at least the melting temperature of the thermally reversible barrier.

In some illustrative embodiments, this present invention relates to an assay device wherein the thermally reversible barrier opens to allow a fluid applied to the porous substrate to flow from one assay area to another assay area when heated to at least the melting temperature of the thermally reversible barrier, and wherein the thermally reversible barrier stops a sample fluid applied to the porous substrate substantially from flowing from one assay area to another when the thermally reversible barrier is cooled to a temperature below the melting temperature of the thermally reversible barrier.

In some illustrative embodiments, this present invention relates to an assay device wherein the thermally reversible barrier stops a fluid applied to the porous substrate substantially from flowing from one assay area to another assay area when the thermally reversible barrier is maintained at a temperature lower than its melting temperature, and wherein the thermally reversible barrier opens to allow a sample fluid applied to the porous substrate to flow from one assay area to another when the thermally reversible barrier is heated to a temperature at least above the melting temperature of the thermally reversible barrier.

In some illustrative embodiments, this present invention relates to an assay device wherein the thermally reversible barrier blocks the flow of a fluid applied to the porous substrate from a first assay area to a second assay area at a first temperature and allows the flow of a fluid applied to the porous substrate from one assay area to a second assay area at a second temperature.

In some illustrative embodiments, this present invention relates to an assay device wherein the thermally reversible barrier blocks the flow of a fluid applied to the porous substrate from a first assay area to a second assay area at a first temperature and allows the flow of a fluid applied to the porous substrate from one assay area to a second assay area at a second temperature, wherein said first temperature is below 65° C. and said second temperature is at least 68° C. whereby said thermally reversible barrier is blocking substantially fluid flow at the initial temperature and subsequently allows the fluid to flow at the second temperature.

In some illustrative embodiments, this present invention relates to an assay device wherein the thermally reversible barrier blocks the flow of a fluid applied to the porous substrate from a first assay area to a second assay area at a first temperature and allows the flow of a fluid applied to the porous substrate from one assay area to a second assay area at a second temperature, wherein said first temperature is at or below 41° C. and said second temperature is at or above 48° C. whereby said thermally reversible barrier is substantially blocking fluid flow at the initial temperature and subsequently allows the fluid to flow at the second temperature.

In some illustrative embodiments, this present invention relates to an assay device wherein the thermally reversible barrier allows a sample fluid applied to the porous substrate to flow from one assay area to another when the thermally reversible barrier is maintained at a temperature lower than its melting temperature, and wherein the thermally reversible barrier closes to substantially stop a fluid applied to the porous substrate from flowing from one assay area to another assay area when the thermally reversible barrier is heated to a temperature at least above the melting temperature of the thermally reversible barrier.

In some illustrative embodiments, this present invention relates to an assay device wherein the thermally reversible barrier allows the flow of a fluid applied to the porous substrate from one assay area to a second assay area at a first temperature and blocks the flow of a fluid applied to the porous substrate from a first assay area to a second assay area at a second temperature.

In some illustrative embodiments, this present invention relates to an assay device wherein the thermally reversible barrier allows the flow of a fluid applied to the porous substrate from one assay area to a second assay area at a first temperature and blocks the flow of a fluid applied to the porous substrate from a first assay area to a second assay area at a second temperature, wherein said first temperature is at or below 65° C. and said second temperature is at or above 68° C. wherein said thermally reversible barrier allows the fluid to flow at the initial temperature and subsequently substantially blocks fluid flow at the second temperature.

In some illustrative embodiments, this present invention relates to an assay device wherein the thermally reversible barrier allows the flow of a fluid applied to the porous substrate from one assay area to a second assay area at a first temperature and blocks the flow of a fluid applied to the porous substrate from a first assay area to a second assay area at a second temperature, wherein said first temperature is at or below 41° C. and said second temperature is at or above 48° C. wherein said thermally reversible barrier allows the fluid to flow at the initial temperature and subsequently substantially blocks fluid flow at the second temperature.

In some illustrative embodiments, this present invention relates to an assay device wherein the thermally reversible barrier comprises a phase change material, such as agarose, fatty acids, gelatin, wax, or a combination thereof.

In some illustrative embodiments, this present invention relates to an assay device wherein the assay device is a paper-based nucleic acid amplification and detection assay device.

In some illustrative embodiments, this present invention relates to a paper-based nucleic acid amplification assay device wherein the assay device is for the detection of virus, such as HIV, Zika Virus, and the like.

In some illustrative embodiments, this present invention relates to a paper-based nucleic acid amplification assay device wherein the assay device is for the detection of bacterial pathogens, such as *E. coli. Vibrio cholerae, Staphylococcus aureus.* Group B *streptococci, Klebsiella pneumoniae, Bordetella perlussis, Bordetella bronchiseptica*, and the like.

In some illustrative embodiments, this present invention relates to a paper-based nucleic acid amplification assay device wherein the assay device is for the detection of malaria parasites or the like.

In some other illustrative embodiments, this present invention relates to a method for testing a sample for the presence or absence of a nucleic acid comprising the steps of:
  a. providing an assay device comprising a porous substrate comprising a sample application area, an amplification area, and a detection area wherein the sample application area and amplification area are separated by a first thermally reversible barrier and the amplification area and detection area are separated by a second thermally reversible barrier;
  b. applying a sample to the sample application area;
  c. allowing the sample to flow from the application area to the amplification area;
  d. heating the first thermally reversible barrier to a temperature above the melting point of the first thermally reversible barrier whereby blocking the flow of the sample from the amplification area back into the sample application area when cooled to ambient temperature;
  e. amplifying a nucleic acid of the sample optionally at an elevated temperature;
  f. heating the second thermally reversible barrier to a temperature at or above the melting temperature of the barrier whereby allowing the sample to flow from the amplification area to the detection area; and
  g. visualizing the presence or absence of the nucleic acid in the sample.

In some illustrative embodiments, this present invention relates to a method for testing a sample for the presence or absence of a nucleic acid disclosed herein, wherein the first and the second thermally reversible barriers comprise a material of different melting point.

In some illustrative embodiments, this present invention relates to a method for testing a sample for the presence or absence of a nucleic acid using an assay device disclosed herein, wherein the first and the second thermally reversible barriers of said device comprise a material of the same melting point.

In some illustrative embodiments, this present invention relates to a method for testing a sample for the presence or absence of a nucleic acid using an assay device disclosed herein, wherein said assay device further comprises an amplification reagent area, the amplification reagent area being adjacent to the amplification area and being separated from the amplification area.

In some illustrative embodiments, this present invention relates to a method for testing a sample for the presence or absence of a nucleic acid using an assay device disclosed herein, wherein the method further comprises the step of folding over the amplification reagent area allowing the amplification reagents to diffuse into the amplification area.

In some illustrative embodiments, this present invention relates to a method for testing a sample for the presence or absence of a nucleic acid using an assay device disclosed herein, the method comprising the steps of:
  a. providing an assay device comprising a porous substrate comprising a sample application and amplification area, a waste area, and a detection area wherein the sample application area and amplification area are separated by a first thermally reversible barrier and the amplification area and detection area are separated by a second thermally reversible barrier;
  b. applying a sample to the sample application area;
  c. allowing the sample liquid to flow from the sample application area to the waste area;
  d. heating the first thermally reversible barrier to a temperature above the melting point of the first thermally reversible barrier whereby blocking the flow of the sample from the waste area back into the sample amplification area when cooled to ambient temperature;
  e. amplifying a nucleic acid of the sample optionally at an elevated temperature;
  f. heating the second thermally reversible barrier to a temperature at or above the melting temperature of the barrier whereby allowing the sample to flow from the amplification area to the detection area; and
  g. visualizing the presence or absence of the nucleic acid in the sample.

In some illustrative embodiments, this present invention relates to a method for testing a sample for the presence or absence of a nucleic acid using an assay device disclosed herein, wherein the method further comprises the step of folding over the amplification reagent area allowing the amplification reagents to diffuse into the amplification area.

In some illustrative embodiments, this present invention relates to a method for testing a sample for the presence or absence of a nucleic acid using an assay device disclosed herein, wherein said assay device comprises a plurality of thermally reversible barriers and a plurality of assay areas.

In some illustrative embodiments, this present invention relates to a method for testing a sample for the presence or absence of a nucleic acid using an assay device disclosed herein, wherein said assay device further comprises an amplification reagent area, the amplification reagent area being adjacent to the amplification area and being separated from the amplification area.

In some illustrative embodiments, this present invention relates to a method for testing a sample for the presence or absence of a molecule comprising the steps of:
  a. providing an assay device comprising a porous substrate comprising a sample application area, an amplification reagent area, and a detection area wherein the sample application area and detection area are separated from the amplification reagent area by a thermally reversible barrier,
  b. applying a sample to the sample application area;
  c. allowing the sample liquid to flow from the sample application area to the detection area;
  d. heating the thermally reversible barrier to a temperature above the melting point of the thermally reversible barrier whereby allowing the flow of the amplification reagents from the amplification reagent area into the detection area; and e. visualizing the presence or absence of the nucleic acid in the sample.

The present invention can be better understood by reference to the following examples which are offered by way of illustration. The present invention is not limited to the examples given herein.

Example 1: HIV Assay

Sample preparation: Size Filtration and Thermal Virion Lysis: HIV-1 virions are captured from a 100 μL whole blood sample by adding the blood to a glass fiber pre-filter which is designed to capture red blood cells and other particles greater than 0.6 μm diameter, while allowing plasma to flow to the reaction pad. Virions themselves are captured in polyether sulfone filter designed to filter particles larger than 0.1 μm (HIV is a 0.12 μm particle). Excess liquid is absorbed in a waste pad. Thermal lysis is used during the isothermal amplification reaction to denature the viral capsids and release RNA. The 65° C. isothermal amplification reaction temperature is greater than the 56° C. required for HIV denaturation and thermal lysis of bacteria using this technique has been previously achieved (Isreal-Ballard, et al. *J. Acquir. Ummune Defic. Syndr.* 2007; 45:318-323; Linnes, et al. *RSC Adv.* 2014: 4(80):42245-42251). Viral capture and blood cell filtration are visually evaluated using transmission electron microscopy of the filter membranes while reverse transcription polymerase chain reaction (RT-PCR) is used to detect viral RNA in each filter/capture membrane, the starting sample, and the waste pad (or sink).

Wax Printed Fluidic Control Valves: Traditional microfluidic devices require complex injection molded components to provide pumping and valve actuation that moves fluids from one reaction step to the next. In ultra-low cost paper-based devices, passive wicking of fluid through a paper network is performed by the membrane itself. However, to date, paper-based valves that facilitate fluidic control are not compatible with the extended temperatures and times required for nucleic acid amplification. Instead, wax-printed valves on the porous membrane itself are assembled to control fluidics that stop/start fluid flow during blood filtration, pathogen capture, isothermal amplification, and quantitative detection. These valves are generated by printing a band of wax onto a porous nitrocellulose membrane that connects the sample capture zone to the waste and detection pads. This wax band lies on the surface of the membrane and does not initially interfere with fluid wicking through the pores.

When heated by low-power, thin-film resistive heaters, the wax melts into the membrane, filling the pores and blocking fluid flow: a closed valve. In early tests, it has been observed that by re-heating a previously closed valve, the valve may be opened as sample fluid pushes the melted wax out of its way to flow past. Wax valve thickness, heating temperature and time, and addition of surfactants are optimized for fluidic control.

Isothermal Amplification via Ink-jet Printed Reagents: Reverse transcription loop mediated isothermal amplification (RT-LAMP) is an isothermal technique that includes both reverse transcription of RNA to DNA and amplification of DNA in a single 65° C. reaction. Using a bioreagent printer adapted from ink-jet printing technology, a U.S. Center for Disease Control validated RT-LAMP is modified and used to print the associated enzymes, salts, and nucleotides onto a paper matrix that will be rehydrated with the filtered sample containing the HIV-1 virus (Curtis, et al. *J. Virol. Methods* 2008: 151(2): 264-70). The reaction chamber, reagent concentration, drying temperature, humidity, and drying time are sequentially optimized in order to obtain a limit of detection of 100 viral particles from a 100 μL whole blood sample. Strategies to reach this detection limit include combinatorial printing of the reagents to prevent early mixing and optimize the stability of reagents embedded in the membrane. The protective effect of printing the RT-LAMP reagents directly into the filtration membranes is determined by evaluating their performance over time with both wet and dry reagents using a real-time thermal cycler to determine the time to amplification (defined as the time required to reach the cycle threshold). To further detect amplicons in a method compatible with the paper device of the present invention, the forward and reverse loop primers are tagged with fluorescein isothiocyanate (FITC) and biotin, respectively, to permit visual detection on lateral flow detection strips. Currently, inexpensive qualitative strips detecting FITC-tagged nucleotides are commercially available worldwide and are utilized as a proof-of-concept in the paper-fluidic device.

Device Integration: The device as shown in FIG. 2 is surrounded in pressure sensitive adhesive and has a symmetric hole in which the blood filter and polyether sulfone capture matrix are placed. The sample is added and the open sample-to-waste valve allow fluid to flow through to the waste pad (FIG. 2, step 1). The user folds the amplification pad with printed RT-LAMP reagents onto the capture matrix and the device is then heated beneath valve 1 which closes and prevents backflow of waste fluid into the amplification sample (FIG. 2, step 2). The amplification pad is heated to about 65° C. for RT-LAMP (FIG. 2, step 3). The second valve is then opened by directional heating and the sample flows to the detection pad for visual verification of pathogens present in the nucleic acid (FIG. 2, step 4).

Example 2: Temperature Controlled Valve Open and Close—a Preliminary Study

There were a few assumptions and approximations made to support this preliminary experiment. The fluid source was assumed to be unlimited and the evaporation was considered to be negligible under good sealing condition. In order to simulate these approximations, the source pad was kept completely wet during the experiment. It was also assumed that the melting temperature would be high enough so that it would not melt at all at 65° C. To simulate this situation using a wax with a melting point of 68° C., the temperature at first 20 mins (heating process) was set at room temperature.

Material and Experimental Setup

Figure 5:
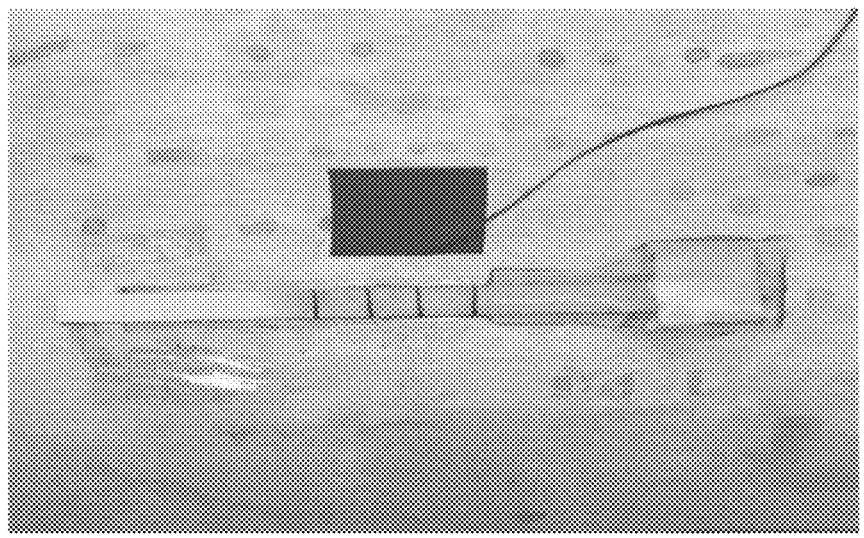
FIG. 5 is a photograph showing the ability of water to flow on a porous hydrophilic substrate over a thermally reversible barrier when the temperature is above the melting temperature of the thermally reversible barrier.
Figure 3:
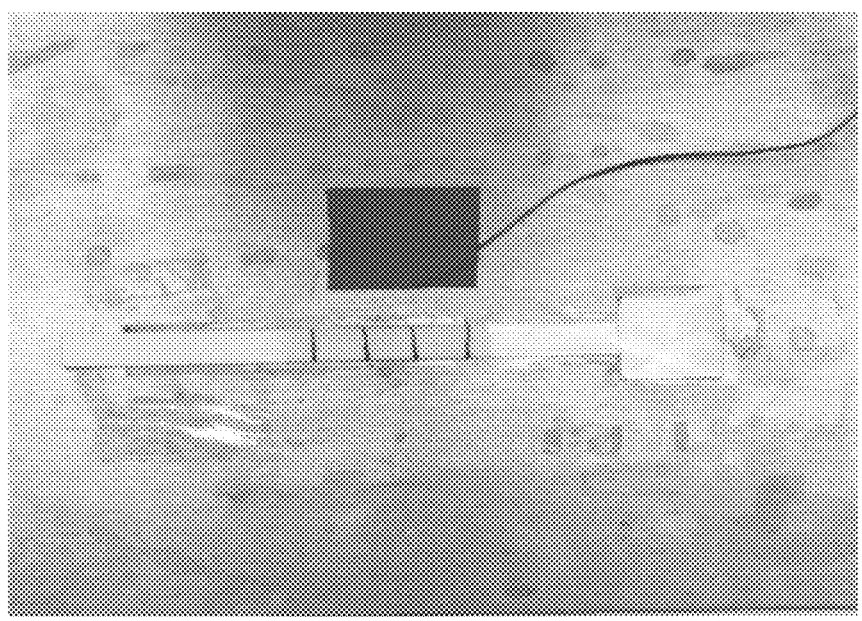
FIG. 3 is a photograph showing a prototype of a thermally reversible barrier of the present invention.

The paper strip was a 6 mm wide strip made from 3 MM paper and the source pad was a 2×2 cm$^2$ paper pad made from GB003 paper. As shown in FIG. 3, a thin aluminum plate was placed on top of the hot plate and the strip was taped on the aluminum plate by double-sided sticky tape. There were four lines drawn on the strip. The two in the middle indicated where the solid wax was placed and the other two indicated the farthest place where the melted wax had reached. In order to prevent evaporation, single-sided laminating plastic was used to cover source pad and the part of paper strip before the wax. A thermocouple was attached to the aluminum plate with a red tape as shown in FIGS. 3, 4, and 5.

Experiment Procedure: The 0.5 cm area between the two middle lines with wax was covered and then the hot plate was turned on to heat the aluminum plate up to about 70° C.

until the wax was completely melted and absorbed by the paper. One thing that should be mentioned is that the surface temperature of the hot plate was much lower than what it appears on the screen, and it was set to about 100° C. to get that actual temperature to about 70° C. The surface temperature of the aluminum was measured by the thermalcouple attached. One milliliter of water colored with gel food color was applied onto the source pad when the plate was cooled to room temperature. Finally, the hot plate was again turned on to reach about 70° C. The whole process was recorded with a phone camera.

Figure 4:
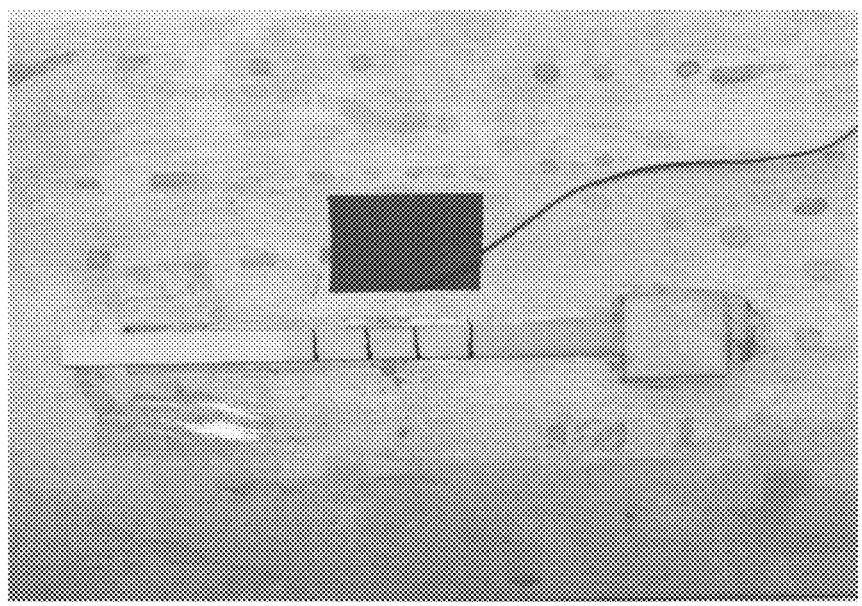
FIG. 4 is a photograph showing the ability of a thermally reversible barrier to block the flow of water on a porous hydrophilic substrate when the temperature is below the melting temperature of the thermally reversible barrier.

FIG. 4 shows how far the fluid reached after about 20 min at room temperature. This result showed that the wax has the ability to completely stop the water flow. It should be noted that the bottom left corner showed fluid after 20 min. There may be various reasons for that but the main reason is that since the wax only covered the center area, the fringe of the "wax area" was not sealed as well as it could be.

FIG. 5 shows the result 2 min after the aluminum plate was reheated up to about 70° C. This result proved that the water could push the melted wax away. In other words, the wax could be used as a valve if it is melting temperature was high enough.

Example 3: Valve Fabrication

Open valves were prepared by printing solid wax-ink containing pigment and paraffin wax (Black ColorQube ink. Xerox, Norwalk, CT) onto nitrocellulose (NC) and cellulose (Chr1) membranes (FFI20HP & cellulose, GE Healthcare. Pittsburgh, PA) using a Xerox ColorQube 8570 (Norwalk, CT). The membranes were cut into 4 min by 20 mm strips on a Silver Bullet vinyl cutter with a 45° blade offset and overcut 0.65 mm at 95 mm s$^{-1}$ with a pressure setting of 80 (Silver Bullet Cutters, Apple Valley, MN). Closed wax valves were first prepared in the same manner as the open valves. Membranes were then heated for one (nitrocellulose) or twelve (cellulose) minutes at 80° C. in a table-top oven (VWR, Radnor, PA) and cut into 4 mm by 20 mm strips on the vinyl cutter.

Valve Actuation

Valves were characterized by heating on a 28 Ω, 10 W in$^{-2}$ density polyimide thin-film heater (Cole-Parmer, Vernon Hills, IL) using a 1550 B&K Precision Power Supply (Yorha Linda, CA), and local temperature was recorded in real-time using a temperature data logger (Lascar, Erie, PA) with a T-type thermocouple (Omega, Stamford, CT). Previously prepared membrane strips were adhered to the thin-film heater by sandwiching double-sided pressure sensitive adhesive (3M, Maplewood, MN) between the heater and the membranes. The thermocouple was taped to the top face of the thin-film heater in order to detect the local temperature at the valve. The temperature was logged every five seconds. Actuation of the valves was observed by wicking 2% solutions of water soluble colored dye (McCormick, Sparks, MD) through the membrane strips. Wax valves were actuated by applying current to the thin-film heater. A Canon EOS Rebel T3i camera (Canon, Melville, NY) was used to image the fluid flow at five second time-lapse intervals.

Open-to-Closed Valve Characterization

Open valves were closed in situ by locally heating the valve. Twenty microliters of blue dye solution was applied upstream of an open valve and observed to flow past the valve. To determine the amount of time required for the wax-ink to permeate the wet membrane, 0.21 amps was applied to the thin-film heater for 30-45 seconds. After an additional 30 seconds of incubation at room temperature, red dye solution was applied upstream of the actuated valve. Valve closure was confirmed by the absence of red fluid wicking past the valve.

Closed-to-Open Valve Characterization and Tuning

To determine the current required to actuate a closed-to open valve, a 0.1 mm (nitrocellulose) or 1 mm (cellulose) width closed wax valve was fabricated as described in Valve fabrication and adhered to a thin-film heater as described in Valve actuation. Twenty microliters of blue solution was pipetted onto the membrane and observed for 20 minutes to ensure that no liquid wicked past the closed valve. The local temperature beneath the closed valve was then increased by applying 0.21 amps to the thin-film heater for 2 minutes. The temperature at which the dye solution began to wick past the valve was recorded.

To meet the time constraints of varying assays, the amount of time required to open valves was determined for valve widths between 0.1 and 10 mm. Closed valves were fabricated as described in Valve fabrication and adhered to a thin-film heater as described in Valve actuation. Twenty microliters of blue solution was pipetted onto the membrane and was observed for 20 minutes as described above. The local temperature beneath the closed valve was then increased by applying 0.21 amps to the thin-film heater. The amount of heating time required for the sample to begin to flow past the valve was recorded. The valve was heated for an additional twenty seconds and the flow rate past the valve was determined by plotting distance wicked versus time.

To characterize the maximum fluid release through a valve, a 0.1 mm (nitrocellulose) or 1 mm (cellulose) closed valve was heated for about 25 (nitrocellulose) or 14 (cellulose) seconds to initially open the valve and then an additional 15-30 seconds. Closed valves were fabricated as described in Valve fabrication and adhered to a thin-film heater as described in Valve actuation. Twenty microliters of blue solution was pipetted onto the membrane and was observed for 20 minutes to ensure fully closed valves did not allow fluid leakage. The local temperature beneath the closed valve was then increased by applying 0.21 amps to the thin-film heater. The flow rate past the valve was determined by plotting distance wicked versus time.

Sequential Valve Actuation

To demonstrate the wax-ink valve's multiple actuation capability, a 0.1 mm open valve was printed onto nitrocellulose membrane. Twenty microliters of blue solution was pipetted onto the membrane and observed to wick past the open-valve. The local temperature beneath the open valve was then increased by applying 0.21 amps to the thin-film heater for 30 seconds. Once the valve reached ambient temperature, twenty microliters of red solution was pipetted onto the membrane and flow was observed to stop at the then closed valve. The valve was actuated once more by opening the closed valve with 0.21 amps applied to the thin-film heater for 20 seconds. The red food coloring was then observed to wick past the valve and the flow rate past the valve was determined by plotting the distance wicked versus time.

To demonstrate wax-ink valve's actuation in series, six 1 mm closed valves were printed onto a cellulose membrane strip. Twenty microliters of blue solution was pipetted onto the membrane and observed to stop at the first valve. The local temperature beneath the first valve was then increased by applying 0.21 amps to the thin-film heater for 15 seconds to release solution through the valve. The solution was observed to stop at the next valve and imaged on an Epson V850 Pro scanner (Long Beach, CA). Solution was similarly released through remaining valves by consecutively heating valves.

Bacterial Cell Culture

E. coli strain C2987 (New England Biolabs, Ipswich. MA) was grown overnight in Lysogeny broth at 37° C. shaken at 250 rpm (Forma Orbital. ThermoFisher Scientific. Wayne, MI). Culture was adjusted to an OD600 (Ultrospec 10, Biochrom, Cambourne, UK) of 1 in deionized (DI) water, representing 5.5×109 cells mL$^{-L}$ as determined by fluorescence microscopy of serially diluted cells.

Integration with Multi-Step LFIAs (Lateral Flow Immunoassays)

Figure 6A:
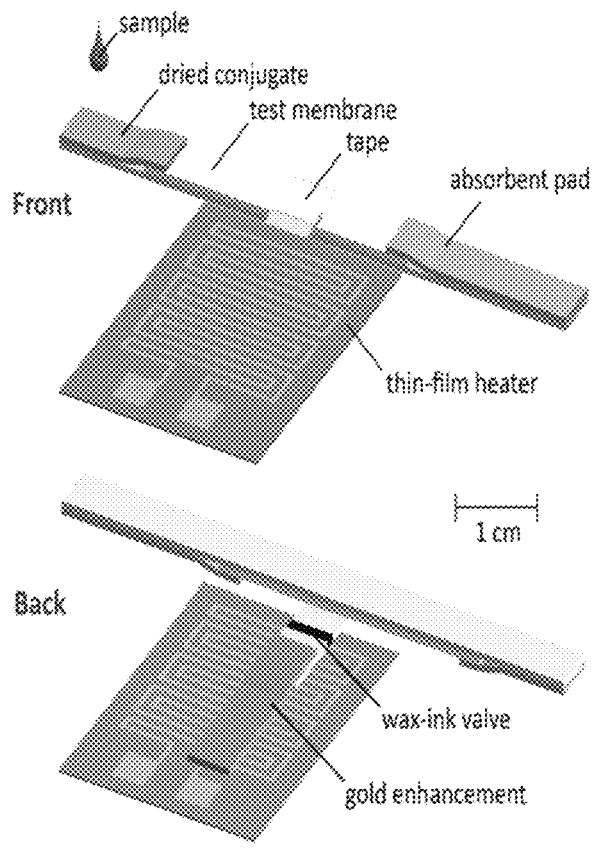
FIG. 6A and FIG. 6B are schematics of a multistep assay enabled by integrating a wax-ink valve into a traditional lateral flow immunoassay and using a thin-film heater as a heat-source to melt the wax.
Figure 6B:
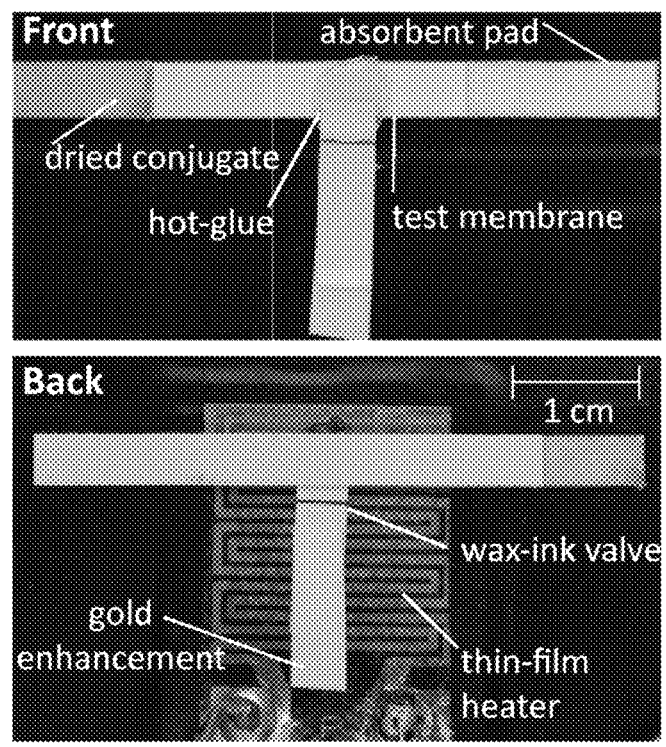

Commercial Rapid Bacteria Pool Water Test strips (Silver Lake Research Corporation, Monrovia, California) were modified into LFIAs by rehydrating the conjugates with 40 µL of DI water for 10 minutes. Rehydrated conjugates were deposited onto 4 by 10 mm strips of Fusion5 conjugate pad (GE Healthcare, Pittsburgh, PA) and dried overnight in ambient conditions. The sample pad of the pool test strips was carefully removed and replaced with the fabricated conjugate pad. Fabricated LFIAs were further modified, as shown in FIGS. 6A (schematic) and 6B (photo), by adhering a previously described (in Valve Fabrication) 4 by 20 mm closed valve in nitrocellulose membrane downstream of the conjugate pad and perpendicular to the test membrane with pressure sensitive adhesive (Dura-Lar, Grafix, Maple Heights, OH) and stacking a 4 by 10 mm strip of Fusion5 upstream of the valve. Lastly, the thin-film heater was adhered to the backside of the valve with pressure sensitive adhesive (3M, Maplewood, MN) directly below the valve.

Forty microliters of E. coli culture diluted in DI water was pipetted onto the conjugate pad of the fabricated LFIA. Forty microliters of Gold Enhance LM solution (Nanoprobes, Yaphank, NY) with 0.015% Tween-20 (Sigma-Aldrich, St. Louis, MO) was simultaneously applied to the Fusion5 pad upstream of the closed valve. After 20 minutes of the E. coli sample wicking through the test strip, 0.21 amps of current was applied to the thin-film heater for 50 seconds to open the valve and release the enhancement solution into the test strip. An additional set of tests strips was left at ambient conditions without actuating the valve and preventing the enhancement solution from wicking through the test strip. All test strips were scanned 40 minutes after initial sample application on an Epson V850 Pro scanner (Long Beach, CA). Test band intensities were analyzed with a custom MATLAB script (C. A. Holstein. *Ph. D Dissertation*, Univ. of Washington, 2015).

Statistical Analysis

To determine if gold enhancement of the LFIA was statistically significant, the LFIA test band intensity of three strips at each E. coli dilution was compared to the averaged single-step or multi-step LFIA experimental negative control test band intensities using a Dunnett's test with alpha set to 0.05. The enhanced and standard LFIA strips were compared to one another at each E. coli dilution using a two-sided T-test with alpha set to 0.05.

Results and Discussion

Valve Actuation

Figure 7:
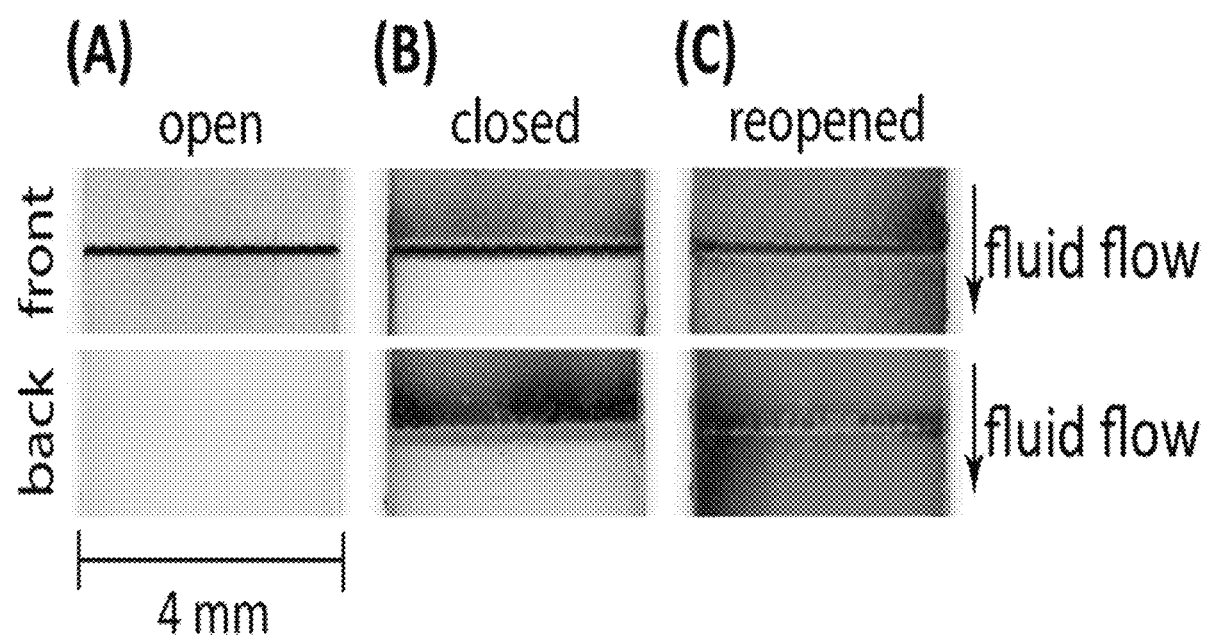
FIG. 7 demonstrates that wax-ink valve rapidly fabricated on nitrocellulose membrane is able to close and reopen. Panel (A) Initially open 0.1 mm valve with wax-ink on surface of the membrane does not block blue fluid passage; Panel (B) Heated valve where wax-ink has permeated into the membrane blocking red fluid passage; Panel (C) Re-heated valve opens again to allow red fluid to pass around the wax.

Thermally actuated wax-ink valves can be quickly incorporated into porous membrane networks for improved paper-fluidic control. Simply by varying the valve width and substrate, fluid flow through the valve can be customized for various assay needs. The printing resolution of the Xerox ColorQube defined the lower limit of our valves width; any black line designed thinner than 0.1 mm was automatically printed at 0.1 mm (FIG. 7A). A 0.1 mm closed valve blocked liquid flow in nitrocellulose for more than twenty minutes with no fluid leakage detected (FIG. 7B). While we see no reason for valves to leak, when we tested for longer than twenty minutes, samples tended to evaporate making it impossible to determine whether fluid flow was prevented by the valve or by inadequate liquid. Notably, 1 mm was the lower limit of valve width on cellulose membrane; fiber length likely permits liquid to pass closed valves thinner than 1 mm.

Open-to-Closed Valve Characterization

As described by Martinez et al., wax ink printed into membranes can be heated to close the porous channels and block fluid flow (A. W. Martinez, et al., *Angew. Chem. Int. Ed.* 2007, 46, 1318-1320). Here, we show that this technique create a thermally actuated valve actuated in situ. Initially open valves actuated in situ required at least 45 seconds of 0.21 amps applied to the thin-film heater in order to close the valves when liquid was present (data not shown). Visual observation of the back face of the membrane confirmed that wax-ink permeated through the membrane (FIG. 7B). Additionally, the lack of red dye flowing past the closed valve confirmed that the valve was fully actuated and closed.

Closed-to-Open Valve Characterization and Tuning

Figure 8A:
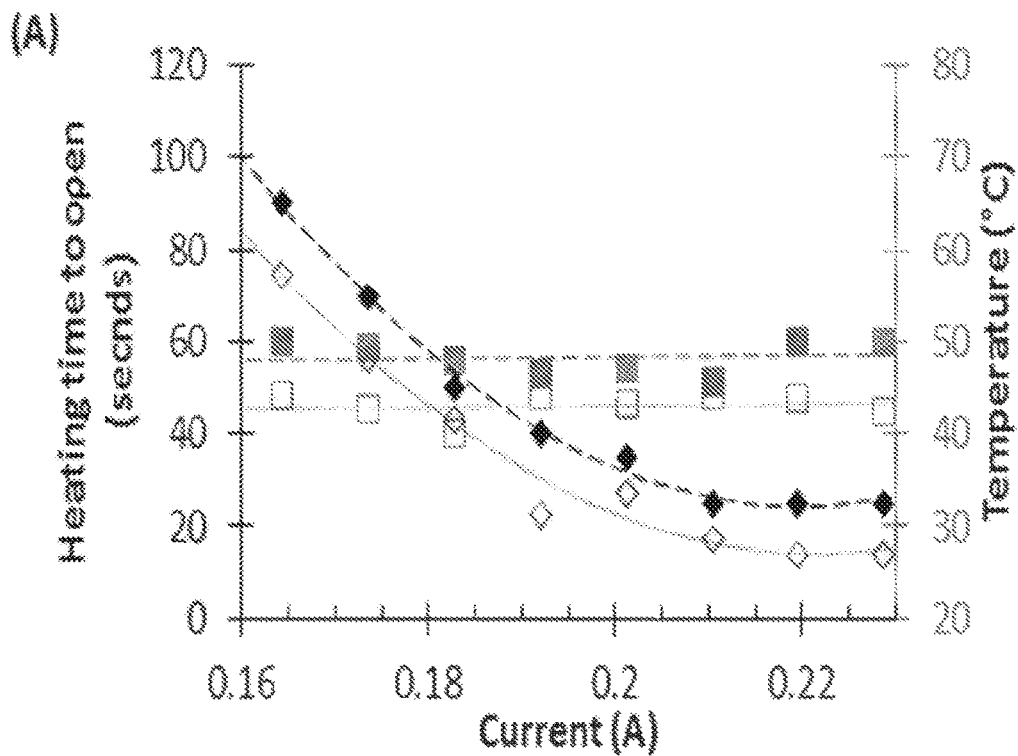
FIG. 8A through FIG. 8D show valve characterization.
Figure 8B:
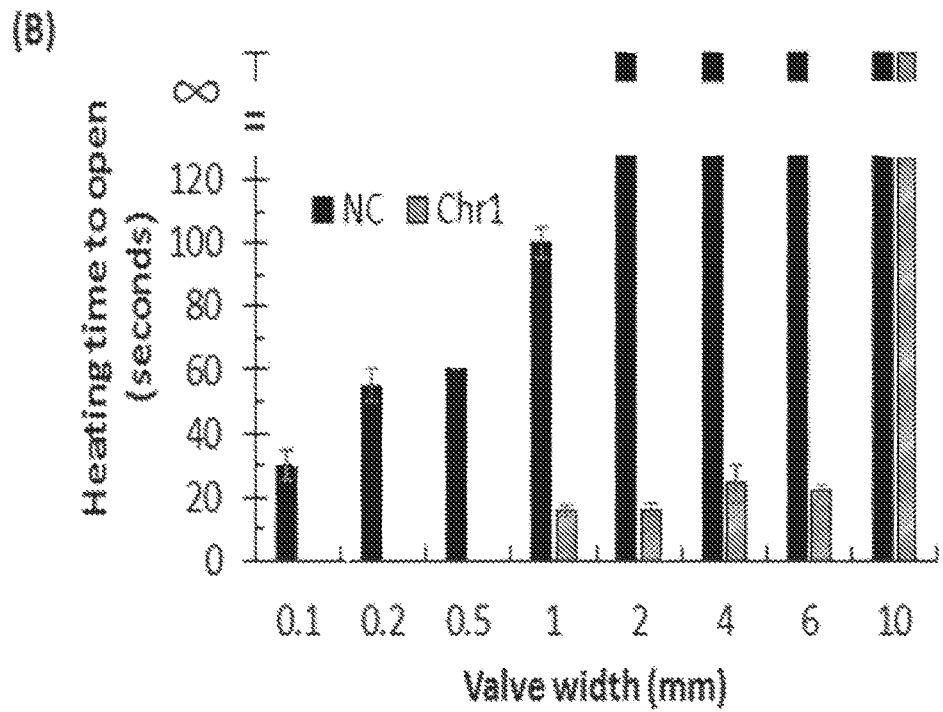
Figure 8C:
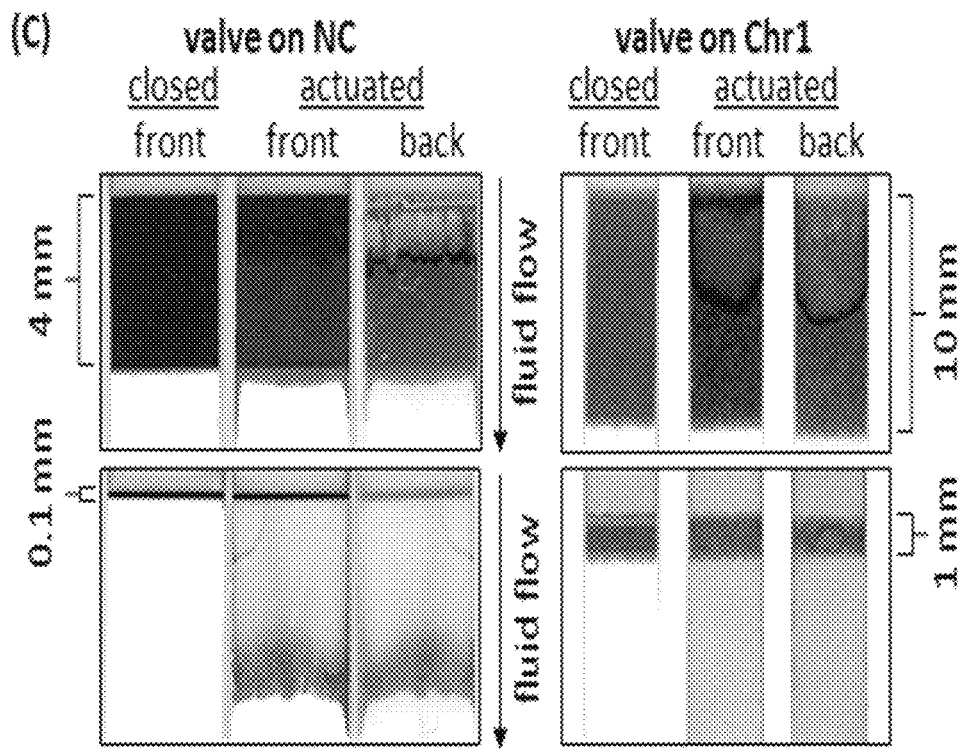

A polyimide thin-film heater was utilized to characterize the opening of a closed valve and to determine the minimal heating (48° C. for 25 seconds on nitrocellulose, 41° C. for 15 seconds on cellulose, FIG. 8A) required to actuate the valve (FIG. 7C). The difference in actuation temperature between nitrocellulose and cellulose may be caused by nitrocellulose's plastic backing that insulates the valve from the heater. As valve width increased, the amount of heating time required to open the valve was also increased (FIG. 8B) and the fluid flow rate past the opened valve decreased. Valves wider than 1 mm (nitrocellulose) and 10 mm (cellulose) were impassable (FIG. 8C), presumably because the fluid pressure gradient created by the membrane capillarity was insufficient to displace the larger quantity of wax. A 4 mm valve was used to demonstrate the fluid front within the wax ink when the liquid was unable to flow through the valve. Similar flow patterns were observed in thinner valves on nitrocellulose: wax-ink melts and flows with a concave profile (FIG. 8C), permitting fluid to pass the edges of the valve until eventually developing a flat fluid front.

If a greater fluid flow rate is required than our 0.1 mm valve enables, then the density of the valve might be printable in grey-scale much as Ouyang, et al, accomplished with their passive, toner-based valves (Y. Ouyang, et al., *Lab Chip*, 2013, 13, 1762-1771). However, in our hands, closed wax valves printed in grey-scale could not prevent fluid flow for as long as the black-wax valves due to inconsistent spacing between the printed wax-ink dots of the valve and thus incomplete valve closure during heating.

Figure 8D:
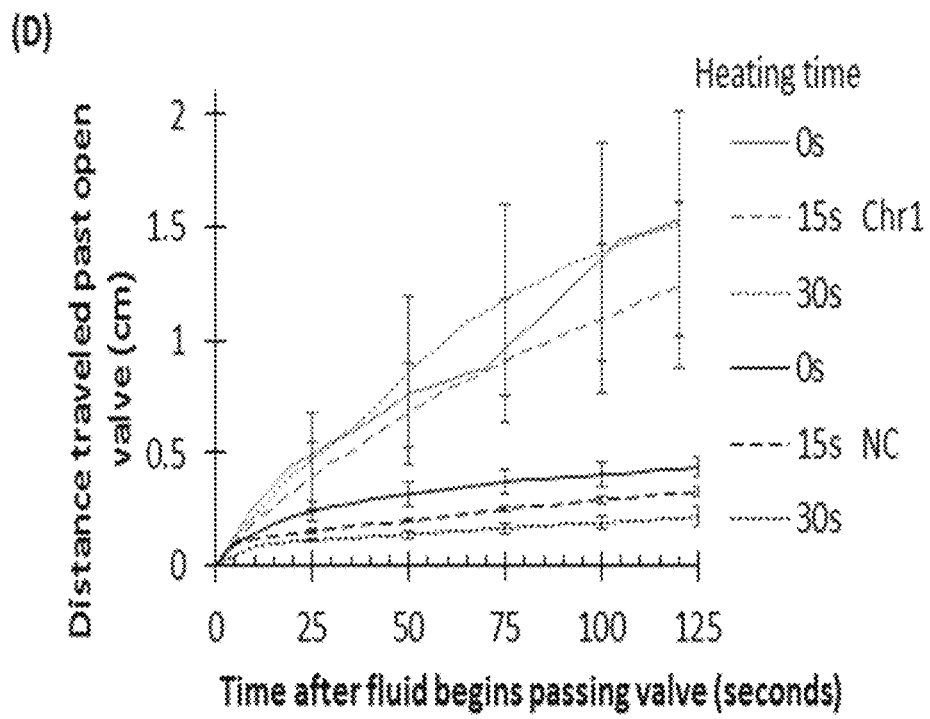

To increase fluid release through closed-to-opened valves, we both decreased valve width to the minimum resolution in each membrane and attempted to increase the length of time that the valve was heated following the initial time required to open the valve (FIG. 8D). Hypothesizing that additional heating would permit complete, vertical heat transfer into the valve, a 0.1 mm (nitrocellulose) and 1 mm (cellulose) valve were heated for an additional 15 and 30 seconds but was found to decrease the total liquid released. The thin-film heater used had a greater surface area than the valve, and therefore the membrane and fluid surrounding the valve also increased in temperature. The surrounding liquid tended to evaporate, which then decreased both the hydraulic pressure and the total amount of liquid available to wick through the membrane. However, cellulose was found to release much more liquid than in nitrocellulose but with greater variance, presumably due to fiber length variance.

Sequential Valve Actuation

Figure 9A:
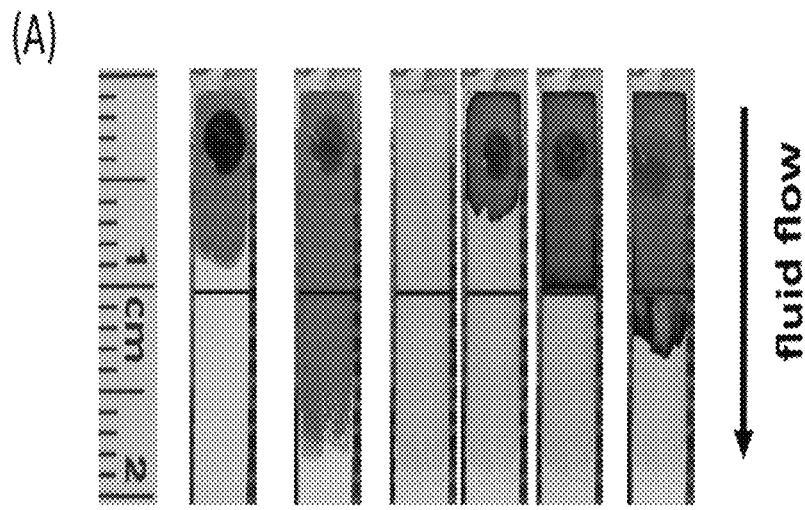
FIGS. 9A and 9B demonstrate multiple actuation of a single valve.
Figure 9B:
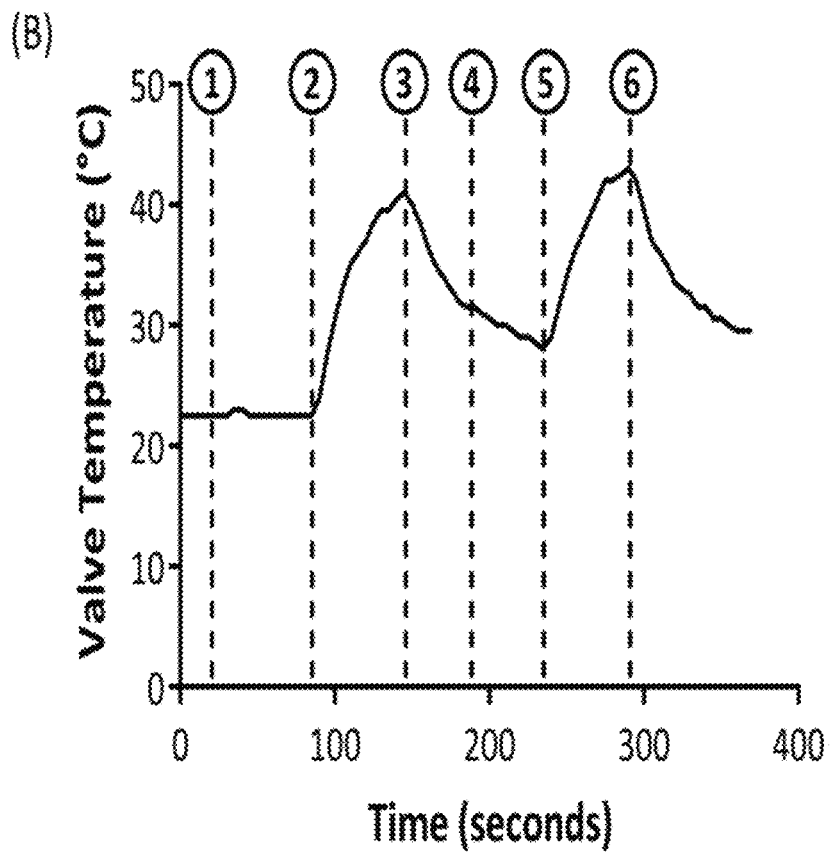

Starting with a valve that was initially open on nitrocellulose, we heated the wax to close the valve, and then re-opened the valve by heating a second time. To our knowledge, this is the first demonstration of a reconfigurable valve allowing multiple actuation steps within a paper-fluidic device. As opposed to previously existing single-use valves in porous membranes, multiple reagents can be released through a single valve as shown in FIGS. 9A and 9B. While we were unable to demonstrate additional actuation beyond the two events shown, even the passage of two distinct solutions improves reaction complexity. Sequential fluid flow through a single valve permits a smaller device foot-print and lowers fabrication costs.

Figure 10:
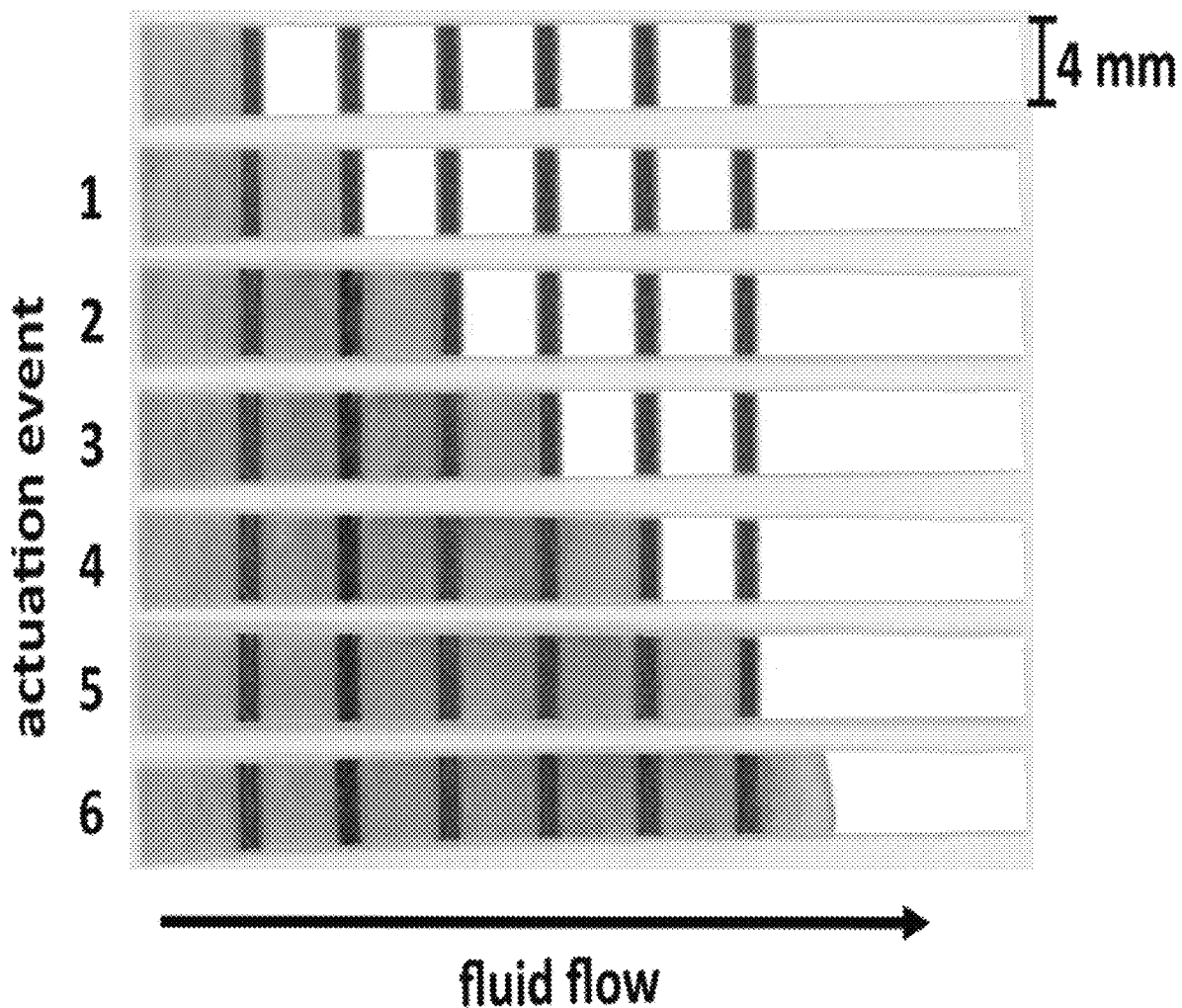
FIG. 10 demonstrates sequential valve actuation. Valves printed on cellulose were consecutively heated to permit controlled, sequential release of liquid into discrete zones, independent of wicking speed. Time between valve heating was approximately 3 minutes.

Additional reaction complexity can be achieved by printing a series of valves on a single membrane strip, as demonstrated in FIG. 10 using cellulose. Consecutive heating of valves permitted the release of liquid into seven discrete zones.

Integration with Multi-Step LFIAs

To demonstrate the application of this wax-ink valve in paper-based diagnostic assays, we modified a standard single-step LFIA into a multi-step LFIA that delivered gold enhancement solution to the test band. Despite previously demonstrating that applying 0.21 amps for 15 seconds was sufficient to release liquid through a closed 0.1 mm valve, no amount of heating was able to release gold enhancement solution alone through the 0.1 mm valve. The surface tension of the gold enhancement solution was likely higher than that of the dyed water used in the characterization experiments. However, by adding 0.015% of Tween-20 to the gold enhancement solution, the closed 0.1 mm valve was able to both block enhancement solution passage for 20 minutes and, upon 0.21 amps of current for 35 seconds, release the enhancement solution into the LFIA. Additives such as surfactants altered the valve characteristics, presumably by lowering the surface tension of the fluid flowing through the valve. This offers additional valve tenability beyond the valve width and heating time, but also requires that valves be further optimized for reagent composition when applied to paper-based assays.

Figure 11A:
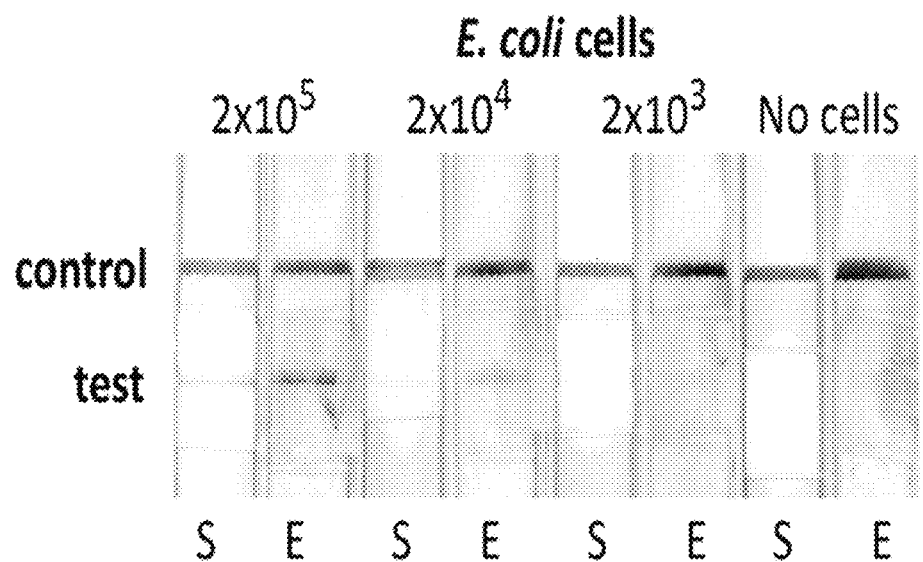
FIGS. 11A and 11B show that thermally actuated wax valves enable multi-step assay.
Figure 11B:
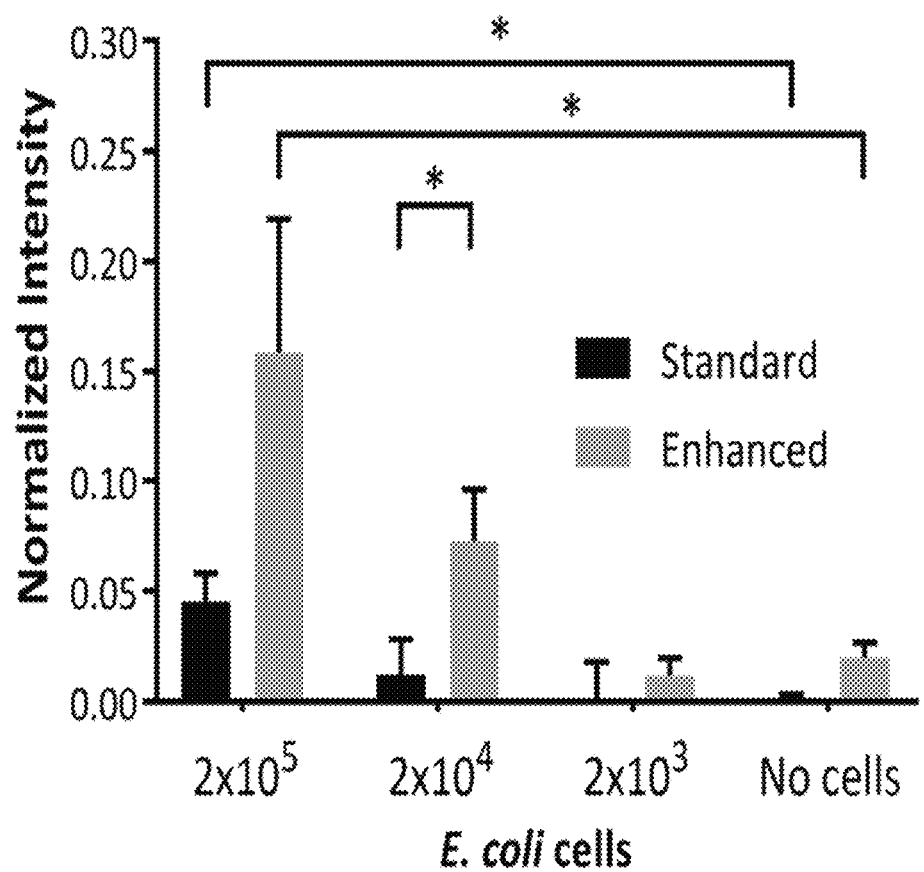

Statistical analysis of the enhanced and standard LFIA test band intensities demonstrated that $2.2\times10^5$ *E. coli* cells were detectable on the LFIAs as compared to the respective negative control bands (FIGS. 11A and 11B). The enhanced strips were also detectable by eye with a statistically significant, 6-fold greater intensity than the standard strips with both $2.2\times10^5$ and $2.2\times10^4$ *E. coli* cells (FIG. 11B). As seen in previously enhanced LFIAs (G. E. Fridley, et al, *Anal. Chem.* 2014, 86, 6447-6453; K. N. Han, et al., *Sci. Rep.*, 2016, 6, 25710), the addition of gold enhancement solution increased intensity in the *E. coli* positive assays, but also increased background intensity. Additional optimization of the enhancement solution volume and timing could further improve the detection limit of the multistep LFIA. While the proof-of-concept required the user to turn on and off the power supply, the multistep assay could be easily modified into a fully automated, single-user step assay with the addition of a simple electronic timer. Nevertheless, the proof-of-concept demonstrated that a wax-ink valve can improve an existing LFIA into a tunable, semi-automated, multistep LFIA for enhanced detection capability.

Smartphone-Controlled Temperature Control of Printed Ink Resistor

Figure 12A:
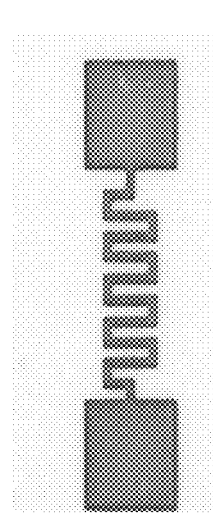
FIG. 12A shows the printed silver-ink resistor for heating.
Figure 12B:
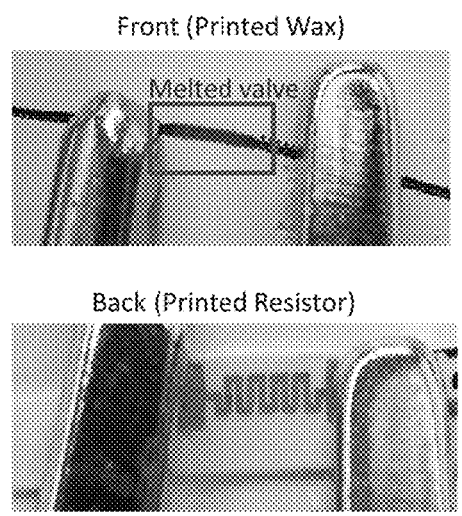
FIG. 12B is a wax-ink valve embedded in a porous membrane connected to a resistor (back) demonstrating that the printed ink-resistor can be used to melt the wax-ink valve from an 'open valve' state to a 'closed valve' state in under 10 minutes using a power setting of 2V and 100 milliamps.
Figure 12C:
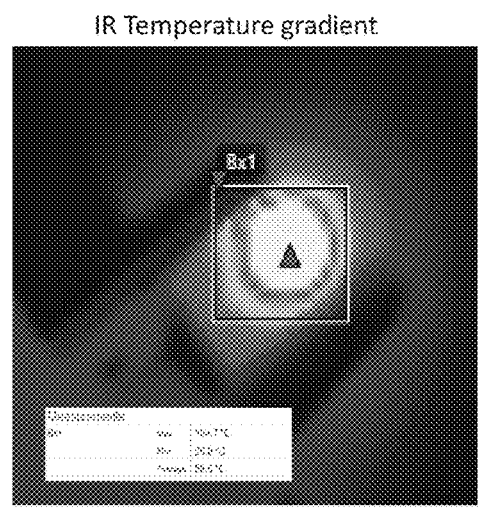
FIG. 12C is an infrared temperature image of the resistor heating the surface of the porous membrane when 100 mA of current was applied.

We have developed a prototype smartphone powered heating unit with three independently controlled temperature zones to heat the valves and amplification assay. FIG. 12A shows the printed silver-ink resistor for heating and FIG. 12B is a wax-ink valve embedded in a porous membrane connected to a resistor (back) demonstrating that the printed ink-resistor can be used to melt the wax-ink valve from an 'open valve' state to a 'closed valve' state in under 10 minutes using a power setting of 2V and 100 milliamps. FIG. 12C is an infrared temperature image of the resistor heating the surface of the porous membrane.

Figure 13:
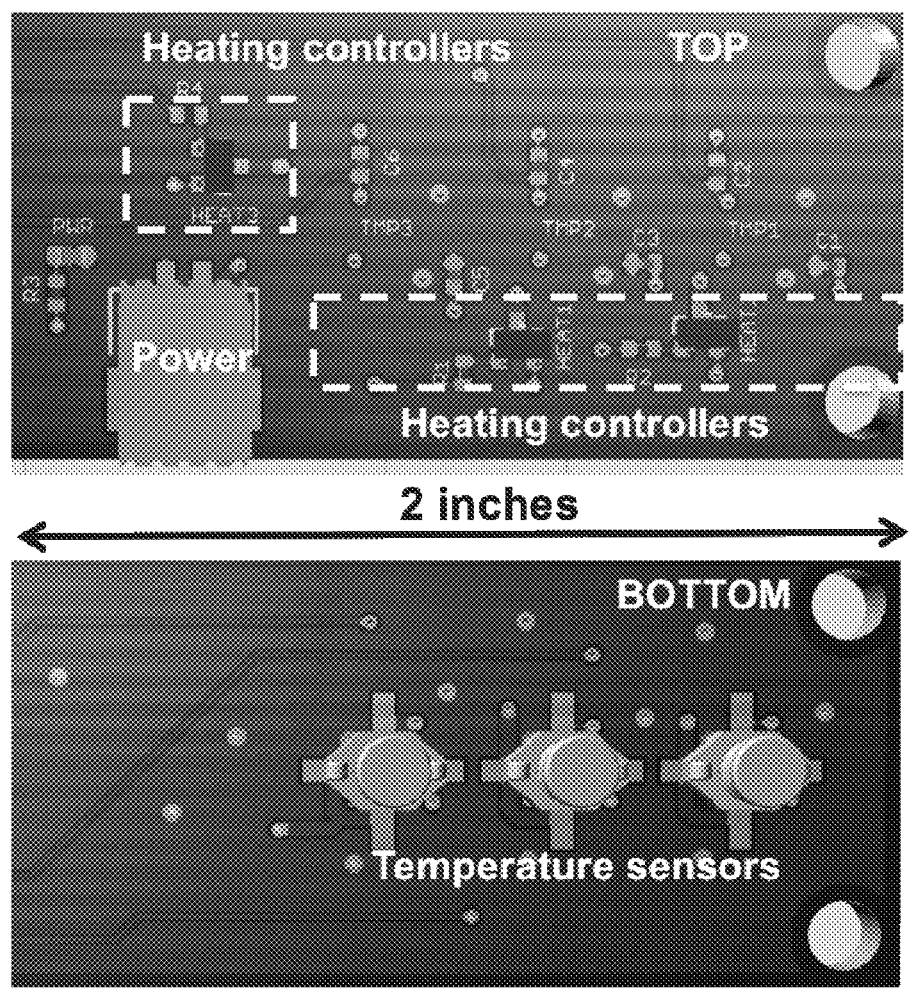
FIG. 13 depicts components of PCB heating unit with an integrated circuit with feedback to control the temperature of the device at three separate locations.
Figure 13:
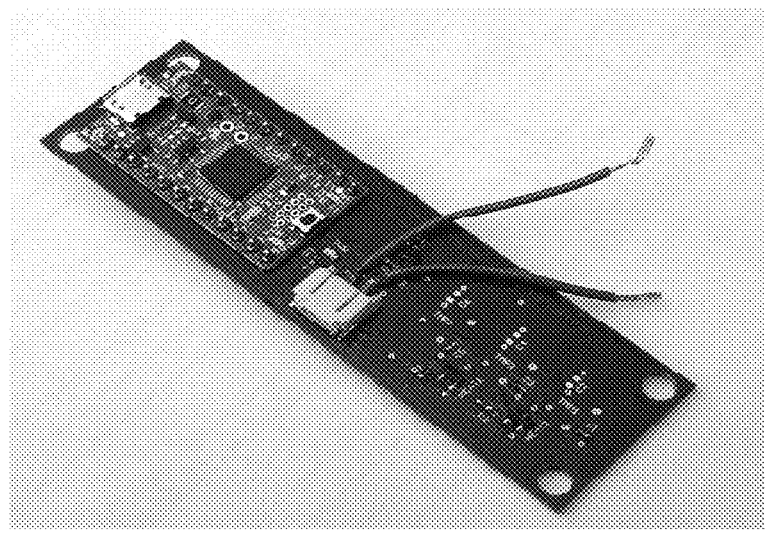

Thermal control is achieved using an SAMD21 microcontroller and TMP37 low voltage temperature sensors (Analog Devices. Norwood, MA). FIG. 13 depicts components of PCB heating unit with an integrated circuit. A microUSB connection in an On-The-Go configuration allows harvesting of the low-power phone output providing the 100 mA current required to heat silver-ink printed resistors to varying temperatures ["USB On-The-Go presents benefits, challenges to power designers," Erik Ogren. AnalogicTech Inc., Sunnyvale, CA www.eetimes.com/document.asp?doc_id=1226476, Accessed Feb. 1, 2017]. The geometry of these resistors can be defined to create varying resistances and heat capacities from the same power source. FIG. 14 shows mobile phone power harvesting and temperature feedback control. FIG. 15 demonstrates that a resistor may heat and maintain temperatures of 37° C. and 65° C. for a sustained 30-minute period. The assay device and the heating components can provide a consistent and reliable temperature control for an extended period of time.

To summarize, we have demonstrated the first use of wax as more than a static barrier to fluid flow. Our reconfigurable wax valves allow both complete fluid obstruction and multiple actuation steps with a single paper-based analytical device. Rapidly fabricated by printing wax-ink onto porous membranes, the tunable wax valves are semi-autonomously and thermally actuated. The utility of these valves is demonstrated by leveraging their controlled fluid release to enhance the detection limit of a traditional LFIA. These wax-ink valves enable increased complexity of fluid operations on paper platforms by permitting sustained reaction incubations times, requiring minimal user involvement, and maintaining low fabrication costs without obstructing downstream chemistries.

Those skilled in the art will recognize that numerous modifications can be made to the specific implementations described above. The implementations should not be limited to the particular limitations described. Other implementations may be possible.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected.

It is intended that that the scope of the present methods and devices be defined by the following claims. However, it must be understood that this disclosure may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims.

The invention claimed is:

1. A valve, comprising:
a thermally reversible barrier;
   a plurality of heating and temperature control components comprising a conductive ink printed resistor operatively positioned proximate said thermally reversible barrier; and
   an associated inlet and an associated outlet across a membrane and configured to selectively operate according to four states: 1) an un-actuated state, where the thermally reversible barrier is placed adjacent the membrane whereby fluid is free to travel across the membrane; 2) an actuated state when temperature of the thermally reversible barrier is raised to a first predetermined threshold, where the thermally reversible barrier melts and permeates into the membrane whereby fluid is stopped from travelling across the membrane, after which the temperature is allowed to be at or below the first predetermined threshold; and 3) an open state when temperature of the thermally reversible barrier is above a second predetermined threshold, where the thermally reversible barrier re-melts whereby fluid in presence of a fluid pressure differential across the membrane is allowed to travel across the membrane.

2. The valve of claim 1, wherein the conductive ink printed resistor is made of silver, carbon, or gold ink.

3. The valve of claim 1, wherein power supply for said conductive ink printed resistor is powered by a phone, tablet, personal computer, or battery, and temperature is regulated via a microcontroller.

4. The valve of claim 1, said first predetermined threshold is about 65° C.

5. The valve of claim 1, wherein said second predetermined threshold is at least about 68° C.

6. The valve of claim 1, wherein the thermally reversible barrier comprises a phase change material, including agarose, fatty acids, gelatin, wax, or a combination thereof.

7. The valve of claim 1, wherein the thermally reversible barrier is positioned between a sample application area and a pad.

8. The valve of claim 7, wherein the pad is one of i) a waste pad, whereby fluid travels from the sample application area to the waste pad, or ii) a buffer pad, whereby fluid travels from the buffer pad to the sample application area.

9. The valve of claim 1, wherein the thermally reversible barrier is positioned between a sample application area and a detection area.

10. The valve of claim 9, wherein the sample application area is adjacent an amplification reagent area.

11. The valve of claim 10, wherein the amplification reagent area and the detection are paper-based nucleic acid components.

12. The valve of claim 11, wherein the paper-based nucleic acid amplification assay device is a detection device for a virus including HIV,Zika Virus, or for a bacterial pathogen including *E. coli, Vibrio cholerae, Staphylococcus aureus*, group B streptococci, *Klebsiella pneumoniae, Bordetella pertussis, Bordetella bronchiseptica*, or for malaria parasites.

* * * * *